(12) United States Patent
Fenteany et al.

(10) Patent No.: US 7,390,826 B2
(45) Date of Patent: Jun. 24, 2008

(54) INHIBITORS OF ANIMAL CELL MOTILITY AND GROWTH

(75) Inventors: Gabriel Fenteany, Oak Park, IL (US);
Arun K. Ghosh, River Forest, IL (US);
Kevin McHenry, Chicago, IL (US);
Audha Ankala, Chicago, IL (US);
Sarosh Anjum, Naperville, IL (US);
Shoutian Zhu, Chicago, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

(21) Appl. No.: 11/259,170

(22) Filed: Oct. 26, 2005

(65) Prior Publication Data

US 2006/0063935 A1 Mar. 23, 2006

Related U.S. Application Data

(62) Division of application No. 10/452,423, filed on Jun. 2, 2003, now abandoned.

(60) Provisional application No. 60/388,141, filed on Jun. 12, 2002.

(51) Int. Cl.
*A61K 31/421* (2006.01)
*C07D 263/18* (2006.01)

(52) U.S. Cl. ........................ 514/376; 548/229

(58) Field of Classification Search ............... 514/376; 548/229
See application file for complete search history.

(56) References Cited

FOREIGN PATENT DOCUMENTS

| EP | 0 818 439 | 1/1998 |
| JP | 9071581 | 3/1997 |
| WO | WO 97/46552 | 12/1997 |
| WO | WO 00/61539 | 10/2000 |
| WO | WO 03/031414 | 4/2003 |

OTHER PUBLICATIONS

C.M. Huwe et al., *Tetrahedron Letters*, vol. 35, No. 51, pp. 9533-9536 (1994).*
K.T. McHenry et al., *ChemBioChem*, vol. 3, pp. 1105-1111 (2002).*
Goldstein, Allan L. *Journal of the National Cancer institute*, vol. 95 (22), Editorials pp. 1646-1647 (2003).*
G. Fenteany et al., *Current Topics in Medicinal Chemistry*, 3, 593-616 (2003).
K.T. McHenry et al., *ChemBioChem*, 3, 1105-1111 (2002).
C.M. Huwe et al., *Tetrahedron Letters*, vol. 35, No. 51, pp. 9533-9536 (1994).
K. Rück et al., *Synthesis*, No. 10, pp. 1018-1028 (1993).
L. Wei et al., *Tetrahedron*, 57, pp. 459-466 (2001).
D.A. Evans et al., *J. Am. Chem. Soc.*, 110, pp. 1238-1256 (1988).
A.S. Raw et al., *Tetrahedron* 56, pp. 3285-3290 (2000).
K.T. McHenry et al., *Chembiochem*, 3, pp. 1105-1111 (2002).
2002:692625 CAPLUS, abstract of Liu, et al. Peptides: The Wave of the Future, Symposium, pp. 862-863 (2001).

* cited by examiner

*Primary Examiner*—Kamal A Saeed
*Assistant Examiner*—Janet L Coppins
(74) *Attorney, Agent, or Firm*—Marshall, Gerstein & Borun LLP

(57) ABSTRACT

Cell motility and growth inhibitors, including compounds of the general structural formula

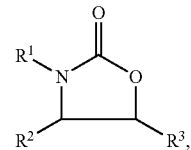

and use of the cell motility and cell growth inhibitors, and pharmaceutically acceptable salts, prodrugs, and solvates thereof, as therapeutic agents, are disclosed.

12 Claims, 8 Drawing Sheets

INHIBITORS OF ANIMAL CELL MOTILITY AND GROWTH

CROSS-REFERENCE TO RELATED APPLICATION

This application is a divisional of U.S. patent application Ser. No. 10/452,423, filed Jun. 2, 2003, now abandoned which claims the benefit of U.S. Provisional Patent Application Ser. No. 60/388,141, filed Jun. 12, 2002.

STATEMENT OF GOVERNMENTAL INTEREST

This invention was made with government support under CA 095177 by the National Institutes of Health. The government has certain rights in this invention.

FIELD OF THE INVENTION

The present invention relates to a series of compounds, to pharmaceutical compositions containing the compounds, and to their use as therapeutic agents. In particular, the present invention relates to compounds that are inhibitors of animal cell motility and growth, and have utility in a variety of therapeutic areas wherein such inhibition is considered beneficial, including the treatment of various cancers.

BACKGROUND OF THE INVENTION

Cell shape change and motility are critical components in a wide range of biological processes in mammals, including embryonic development, tissue repair, angiogenesis, and immune system function. Cell shape change and motility also are involved in pathological events, such as cancer metastasis. While progress has been made in identifying components of signal transduction pathways leading to cell motility, a complete model of the mechanism is still lacking. The precise roles of many proteins implicated in these pathways are not yet elucidated, and a number of mechanisms that cells use for movement may exist.

Cell motility is dependent on regulated actin filament assembly, rearrangement, and disassembly. A large and growing number of proteins are known to regulate and modulate the state of the actin cytoskeleton, and some appear to have partly overlapping functions. For example, actin polymerization and filament assembly can be accomplished through de novo nucleation of new filaments by the Arp2/3 complex or through elongation of existing filaments at free barbed or fast-growing ends, generated by filament severing and/or regulated dissociation of bound barbed-end capping proteins (uncapping). Similarly, multiple routes exist for actin filament bundling, crosslinking, and disassembly (depolymerization).

In addition to these end-point mechanisms of actin dynamics, a number of different upstream signaling pathways leading to changes in the actin cytoskeleton and cell morphology and behavior have become apparent. The small Ras-related GTPases, e.g., Rac, Rho, and Cdc42, in particular, have been implicated in the regulation of the actin cytoskeleton and cell shape, and each plays a distinct and specialized role. Rho proteins are associated generally with formation of contractile actin/myosin bundles, stress fibers, and focal adhesions. Rac proteins particularly are associated with formation of lamellipodia (broad, sheet-like membrane protrusions at the leading edge in the direction of movement). Lamellipodial cell crawling resulting from activation of Rac proteins is considered to be the most prevalent form of animal cell motility. Cdc42 particularly is most associated with formation of filpodia (finger-like membrane protrusions) and the control of cell polarity. The Rho family small GTPases also have roles in other cellular processes, such as control of cell growth and cell-cell adhesion. In addition to these small GTPases, phosphoinositides and calcium are known to regulate actin dynamics and cell migration. However, a comprehensive understanding of the signaling cascades leading to cell motility and the relationship between these regulators remains elusive.

Progress in the art would be facilitated by the availability of effective inhibitors of cell motility. A number of compounds that target actin directly exist. The best known compounds are the cytochalasins, which are cell-permeable destabilizers of actin filaments, and phalloidin, which is a cell-impermeable stabilizer of actin filaments (J. A. Cooper, *J. Cell Biol,* 105 (1987)). In addition, latrunculins are cell-permeable disrupters of actin filaments (I. Spector, *Science,* 219, 493 (1983)). Jasplakinolide is a cell-permeable stabilizer of actin filaments (M. R. Bubb et al., *Chem.,* 269, 14869 (1994)). A few compounds that target proteins upstream of the actin cytoskeleton are known, such as the Rho-kinase inhibitor Y-27632 (M. Uehata et al., *Nature,* 389, 990 (1997), and myosin light chain kinase inhibitors, such as ML-g (M. Saitoh et al., *Biochem. Biophys, Res. Commun.,* 140, 280 (1986)). Recently, a cyclic peptide dimer was discovered that inhibits the activity of N-WASP, a protein involved in Cdc42-mediated actin nucleation by the Arp2/3 complex (J. R. Peterson et al., *Proc. Natl. Acad. Sci. USA,* 98, 10624 (2001)). Nevertheless, there is a dearth of available cell-permeable compounds that affect actin dynamics and cell motility by inhibiting specific components of signaling pathways to the actin cytoskeleton.

Presently, very few specific inhibitors of cell motility are available, even though a great potential exists for such drugs as a complement to existing anticancer therapies. Cell shape change and motility are involved at two rate-limiting steps in cancer progression: angiogenesis (i.e., blood vessel recruitment) and metastasis (i.e., spreading of a tumor from one location in the body to other locations). In combination with cell growth inhibitors, treatment with specific cell motility inhibitors has the potential to provide a more efficacious treatment of a cancer, analogous to the multiple drug approach for treatment of HIV infection and AIDS.

In particular, cell motility inhibitors have potential uses such as, but not limited to, (a) an anticancer drug targeting angiogenesis, (b) an anticancer drug targeting metastasis, and (c) an anticancer drug targeting cell growth.

SUMMARY OF THE INVENTION

The present invention provides compounds of general structural formula (I)

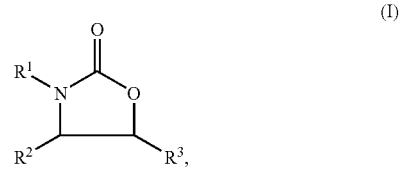

wherein $R^1$ is selected from the group consisting of C(=O) $C_{3-8}$cycloalkenyl, C(=O)C≡C—$R^b$,

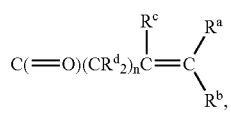

$C_{2-6}$alkenyl, and $C_{2-6}$alkynyl;

$R^2$ is selected from the group consisting of hydro, $C_{1-3}$alkyl, aryl, heteroaryl, $C_{1-3}$alkylenearyl, $C_{1-3}$alkyleneheteroaryl, $C_{3-8}$cycloalkyl, and $C_{3-8}$heterocycloalkyl;

$R^3$ is selected from the group consisting of hydro, $C_{1-3}$alkyl, aryl, and heteroaryl;

$R^a$ is selected from the group consisting of hydro and $C_{1-3}$alkyl;

$R^b$ is selected from the group consisting of hydro, $C_{1-6}$alkyl, $CF_3$, $C_{3-8}$cycloalkyl, $C_{3-8}$heterocycloalkyl, aryl, heteroaryl, S-aryl, O-aryl, $C_{1-3}$alkylenearyl, and $C_{1-3}$alkyleneheteroaryl;

$R^c$ is selected from the group consisting of hydro, $C_{1-3}$alkyl, and fluoro$C_{1-3}$alkyl, or $R^b$ and $R^c$ can be taken together with the carbons to which they are attached to form a five- or six-membered aliphatic ring, optionally containing one or two heteroatoms selected from oxygen, nitrogen, and sulfur;

$R^d$, independently, is selected from the group consisting of hydro, $C_{1-3}$alkyl, and fluoro$C_{1-4}$alkyl; and n is a number 0, 1, or 2, and pharmaceutically acceptable salts, prodrugs, or solvates (e.g., hydrates) thereof.

Another aspect of the present invention is to provide a cell motility and growth inhibitor having a general structural formula (II):

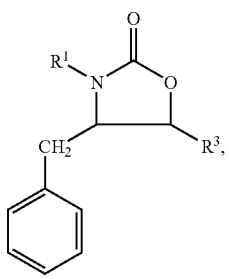

(II)

and pharmaceutically acceptable salts, pro-drugs, or solvates thereof.

Still another aspect of the present invention is to provide a cell motility and growth inhibitor having a general structural formula (III):

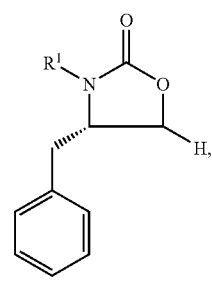

(III)

and pharmaceutically acceptable salts, pro-drugs, or solvates thereof.

Yet another aspect of the present invention is to provide a cell motility and growth inhibitor having a general structural formula (IV):

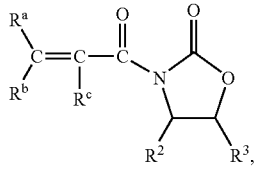

and pharmaceutically acceptable salts, prodrugs, or solvates thereof.

As used herein, the term "a compound of the present invention" is defined as a compound encompassed by general structural formulae (I), (II), (III), and (IV), including, but not limited to, the Examples and specific compounds disclosed herein.

Another aspect of the present invention is to provide a cell motility and growth inhibitor having a biological $IC_{50}$ value of about 50 μM or less, preferably about 25 μM or less, more preferably about 15 μM or less, and most preferably about 1 μM or less, down to about 700 picomolar.

Yet another aspect of the present invention is to provide a composition comprising a compound of the present invention and a physiologically acceptable diluent or carrier.

Another aspect of the present invention is to provide a method of treating an individual suffering from a disease or condition wherein inhibition of cell motility and cell growth provides a benefit, said method comprising administering a therapeutically effective amount of a compound of the present invention, or a composition containing the same, to the individual. The method preferably provides a reversible inhibition of cell motility and growth.

Still another aspect of the present invention is to provide a method of treating an individual suffering from a cancer, said method comprising administration of a therapeutically effective amount of a compound of the present invention, or a composition containing the same, to the individual, either alone or in combination with other cancer treatment agents.

Another aspect of the present invention is to provide a combination therapy comprising administration of therapeutically effective amounts of (a) a compound of the present invention, or a pharmaceutically acceptable salt, prodrug, or solvate thereof, and (b) a second therapeutically active agent, to an individual, simultaneously or sequentially, in the treatment of a disease or condition wherein inhibition of cell growth and cell motility provides a benefit. The disease or condition can be a cancer, and the second therapeutically active agent can be a chemotherapeutic agent or radiation, for example.

In another aspect, the present invention provides a kit for the treatment of cancer comprising a compound of the present invention, or a composition containing the same, packaged with instructions for administration of the compound, or composition, to a mammal, including a human, to treat the cancer. A compound of the present invention and a second therapeutically active ingredient for the treatment of cancer can be packaged together in a single vial, packaged in separate vials, packaged as separate dosage forms, and the like.

These and other aspects of the present invention will become apparent from the following detailed description of the preferred embodiments, taken in conjunction with the figures.

DETAILED DESCRIPTION OF THE PREFERRED EMBODIMENTS

Figure 1A:
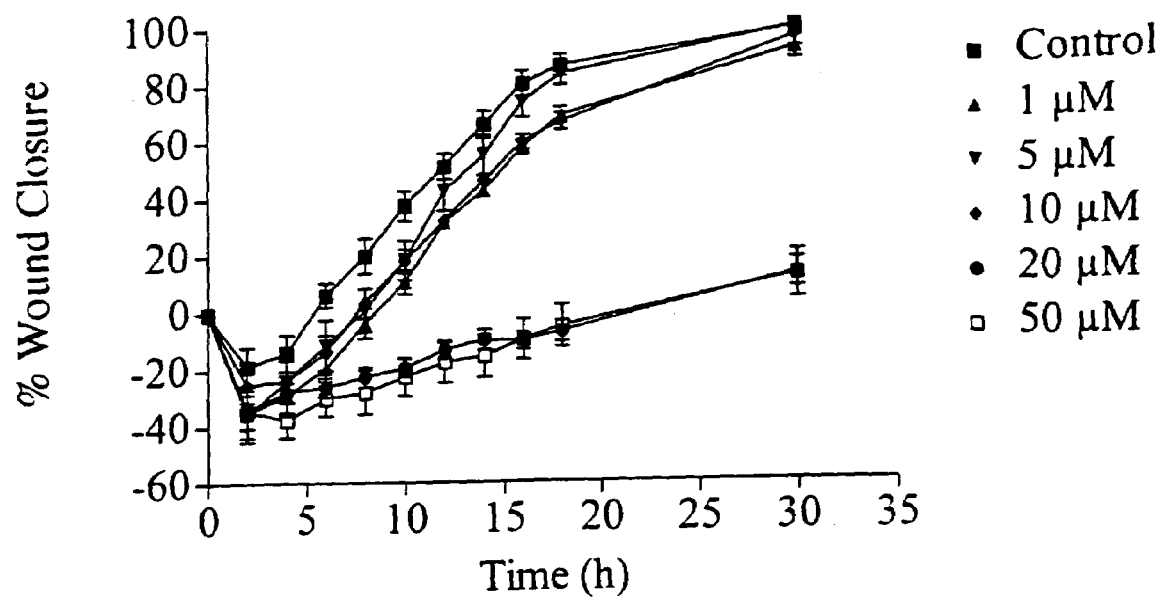
FIG. 1A contains plots of % wound closure in MDCK cell monolayers vs. time after application of different amounts of compound 1.

Inhibitor compounds of the present invention have a general structural formula (I):

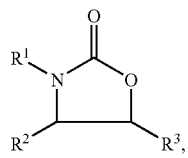

(I)

wherein $R^1$ is selected from the group consisting of C(=O) $C_{3-8}$cycloalkenyl, C(=O)C=C—$R^b$,

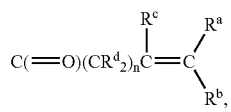

$C_{1-6}$alkyl, $C_{2-6}$alkenyl, and $C_{2-6}$alkynyl;

$R^2$ is selected from the group consisting of hydro, $C_{1-3}$alkyl, aryl, heteroaryl, $C_{1-3}$alkylenearyl, $C_{1-3}$alkyleneheteroaryl, $C_{3-8}$cycloalkyl, and $C_{3-8}$heterocycloalkyl;

$R^3$ is selected from the group consisting of hydro, $C_{1-3}$alkyl, aryl, and heteroaryl;

$R^a$ is selected from the group consisting of hydro and $C_{1-3}$alkyl;

$R^b$ is selected from the group consisting of hydro, $C_{1-6}$alkyl, $CF_3$, $C_{3-8}$cycloalkyl, $C_{3-8}$heterocycloalkyl, aryl, heteroaryl, S-aryl, O-aryl, $C_{1-3}$alkylenearyl, and $C_{1-3}$alkyleneheteroaryl;

$R^c$ is selected from the group consisting of hydro, $C_{1-3}$alkyl, and fluoro$C_{1-3}$alkyl, or $R^b$ and $R^c$ can be taken together with the carbons to which they are attached to form a five- or six-membered aliphatic ring, optionally containing one or two heteroatoms selected from oxygen, nitrogen, and sulfur;

$R^d$, independently, is selected from the group consisting of hydro, $C_{1-3}$alkyl, and fluoro$C_{1-4}$alkyl; and n is a number 0, 1, or 2, and pharmaceutically acceptable salts, prodrugs, or solvates thereof.

In some preferred embodiments, the inhibitor compounds have a general structural formula (II), (III), or (IV):

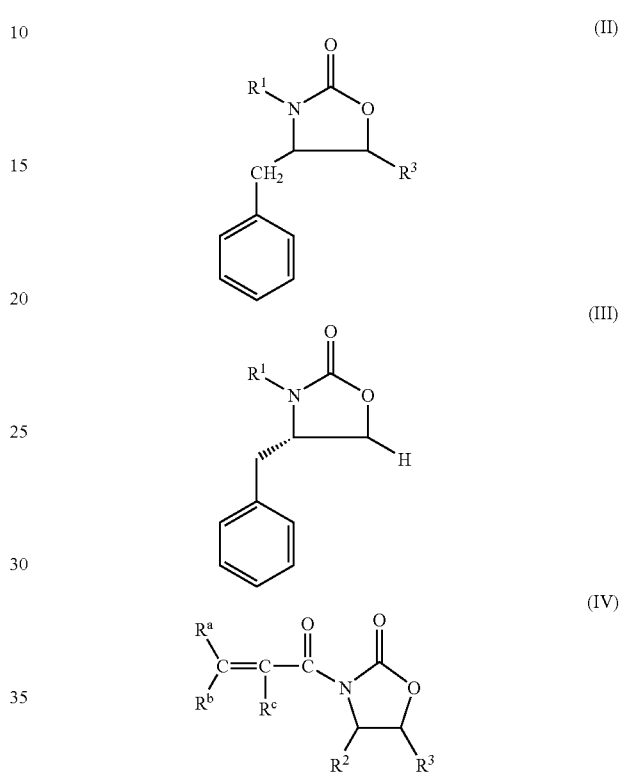

and pharmaceutically acceptable salts, pro-drugs, or solvates thereof.

As used herein, the term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," i.e., a $C_6$-$C_{16}$ bicyclic or polycyclic hydrocarbon group, for example, norbornyl, adamantyl, bicyclo[2.2.2]octyl, bicyclo[2.2.1]heptyl, bicyclo [3.2.1]octyl, or decahydronaphthyl. Alkyl groups can be substituted, for example, with fluoro (F), hydroxy (OH), or amino ($NH_2$) groups.

The term "cycloalkyl" is defined as a cyclic $C_3$-$C_8$ hydrocarbon group, e.g., cyclopropyl, cyclobutyl, cyclohexyl, and cyclopentyl. "Heterocycloalkyl" is defined similarly as cycloalkyl except the ring contains one to three heteroatoms selected from the group consisting of oxygen, nitrogen, and sulfur. Cycloalkyl and heterocycloalkyl groups can be substituted, for example, with one to three groups, independently selected from groups such as $C_{1-4}$alkyl, $C_{1-3}$alkyleneOH, C(=O)$NH_2$, $NH_2$, and OH.

The terms "alkenyl" and "alkynyl" are defined identically as "alkyl," except for containing a carbon-carbon double bond or a carbon-carbon triple bond, respectively. "Cycloalkenyl" is defined similarly to, and is encompassed by, the term cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group.

The term "halo" is defined herein as fluoro, bromo, chloro, and iodo.

The term "haloalkyl" is defined herein as an alkyl group substituted with one or more halo substituents, independently selected from fluoro, chloro, bromo, and iodo. "Halocycloalkyl" is encompassed by the term "haloalkyl," and is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to five, halo, alkyl, alkenyl, cycloalkyl, heterocycloalkyl, aryl, heteroaryl, trifluoromethyl, $OR^b$, $OSi$—$(C_{1-4}alkyl)_3$, $OC(=O)C_{1-4}alkyl$, trifluoromethoxy, $SO_2N(R^b)_2$, $NHSO_2aryl$, $N(R^b)_2$, alkoxyalkyl, haloalkyl, nitro, cyano, acylamino, alkylthio, arylthio, $C(=O)N(R^b)_2$, $C(=O)R^a$, $OC(=O)R^a$, $C(=O)OR^a$, $NR^bC(=O)R^a$, and $OC_{1-3}alkyleneNR^aR^b$. Exemplary aryl groups include phenyl, naphthyl, tetrahydronaphthyl, indenyl, indanyl, biphenyl, chlorophenyl, nitrophenyl, fluorophenyl, methylphenyl, methoxyphenyl, trifluoromethylphenyl, hydroxyphenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, for example, the substituents listed above for aryl groups. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "hydro" is defined as —H.
The term "hydroxy" is defined as —OH.
The term "alkoxy" is defined as —OR, wherein R is alkyl, including cycloalkyl.
The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —$NH_2$, and the term "alkylamino" is defined as —$NR^2$, wherein at least one R is alkyl and the second R is alkyl or hydrogen.

The term "5- or 6-membered aryl or heteroaryl group" as used herein refers to carbocyclic and heterocyclic aromatic groups, including, but not limited to, phenyl, thiophenyl, furyl, pyrrolyl, imidazolyl, pyrimidinyl, and pyridinyl.

The term "acylamino" is defined as $RC(=O)N$—, wherein R is alkyl or aryl.

The term "alkylthio" and "arylthio" are defined as —SR, wherein R is alkyl or aryl, respectively.

The term "alkylsulfinyl" is defined as R—$SO_2$—, wherein R is alkyl.

The term "alkylsulfonyl" is defined as R—$SO_3$—, wherein R is alkyl.

The term "nitro" is defined as —$NO_2$.

The term "trifluoromethyl", is defined as —$CF_3$.
The term "trifluoromethoxy" is defined as —$OCF_3$.
The term "cyano" is defined as —CN.

The carbon atom content of hydrocarbon-containing moieties is indicated by a subscript designating the minimum and maximum number of carbon atoms in the moiety, e.g., "$C_{1-6}alkyl$", refers to an alkyl group having one to six carbon atoms, inclusive.

In the structures herein, for a bond lacking a substituent, the substituent is methyl, for example,

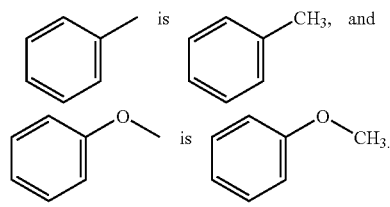

When no substituent is indicated as attached to a carbon atom on a ring, it is understood that the carbon atom contains the appropriate number of hydrogen atoms. In addition, when no substituent is indicated as attached to a carbonyl group or a nitrogen atom, for example, the substituent is understood to be hydrogen, e.g.,

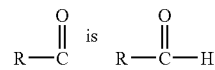

and R—N is R—$NH_2$.

The numbering system for the oxazolidinone ring system is

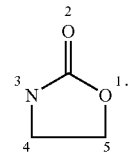

A compound is considered to be a inhibitor of cell motility and cell growth if the compound effectively inhibits cell motility and cell growth at a physiologically compatible concentration. To be useful as a therapeutic compound, the compound also must be nontoxic at such a concentration. Effective inhibition typically is defined as a compound that inhibits cell motility and cell growth by at least 50%, preferably at least 80%, and more preferably at least 90%, at a physiologically compatible concentration.

As discussed in more detail hereafter, cell motility and growth inhibition typically is measured using a dose-response assay in which a sensitive assay system is contacted with a compound of interest over a range of concentrations at which no or minimal effect is observed, through higher concentrations at which partial effect is observed, to saturating concentrations at which a maximum effect is observed. Theoretically, such assays of the dose-response effect of inhibitor compounds can be described as a sigmoidal curve, expressing a degree of inhibition as a function of concentration. The curve also theoretically passes through a point at which the concentration is sufficient to inhibit activity to a level that is 50% that of the difference between minimal and maximal activity in the assay. This concentration is defined as the Inhibitory Concentration (50%) or $IC_{50}$. Comparisons between the efficacy of inhibitors often are provided with reference to comparative $IC_{50}$ concentrations, wherein a higher $IC_{50}$ indicates that the test compound is less potent, and a lower $IC_{50}$ indicates that the compound is more potent, than a reference compound.

An "$IC_{50}$ value" of a compound, therefore, is defined as the concentration of the compound required to produce 50% inhibition of biological activity. Inhibitors of cell motility and cell growth disclosed herein preferably have an $IC_{50}$ value of less than about 50 µM, more preferably less than about 25 µM, and still more preferably less than about 15 µM. Most preferably, a cell motility and cell growth inhibitor of the present invention has an $IC_{50}$ value of less than about 1 µM, down to about 700 picomolar.

Similarly, the potency of inhibitor compounds can be related in terms of the Effective Concentration (50%) or $EC_{50}$, which is a measure of dose-response activity in a cell-based or animal-based model. $EC_{50}$ measurements are useful to relate properties of the compound that can influence its clinical utility, such as compound solubility, ability to penetrate cell membranes, partition coefficient, bioavailability, and the like. Two compounds can exhibit a divergence in comparative $IC_{50}$ and $EC_{50}$ values, i.e., one compound can be more potent in a biochemical assay and the second compound more potent in a cell-based assay simply due to different properties of the compounds.

The term "pharmaceutically acceptable carrier" as used herein refers to compounds suitable for use with recipient animals, preferably mammals, and more preferably humans, and having a toxicity, irritation, or allergic response commensurate with a reasonable benefit/risk ratio, and effective for their intended use.

The term "prodrug" as used herein refers to compounds that transform rapidly in vivo to a compound of the invention, for example, by hydrolysis. Prodrugs of the invention also can be active in the prodrug form. A thorough discussion is provided in Higuchi et al., Prodrugs as *Novel Delivery Systems, Vol.* 14, of the A.C.S.D. Symposium Series, and in Roche (ed), *Bioreversible Carriers in Drug Design,* American Pharmaceutical Association and Pergamon Press, 1987.

In preferred embodiments of the present invention, $R^3$ is hydro, $C_{1-3}$alkyl, or aryl; $R^2$ is hydro, $C_{1-3}$alkyl, aryl, $C_{1-3}$alkylenearyl, or heteroaryl; $R^1$ is C(=O)—$C_{3-8}$cycloalkenyl, C(=O)C≡C—$R^b$, or

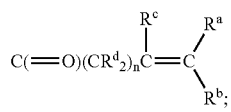

$R^a$ is hydro or $C_{1-3}$alkyl, $R^b$ is hydro, $C_{1-6}$alkyl, $C_{3-8}$cycloalkyl, $CF_3$, aryl, heteroaryl, or S-aryl; $R^c$ is H or $C_{1-3}$alkyl; and n is 0 or 1.

In other preferred embodiments, $R^3$ is hydro or phenyl; $R^2$ is benzyl, hydro, isopropyl, methyl, or phenyl; $R^1$ is C(=O)C≡C—$CH_3$ or

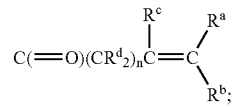

$R^a$ is hydro or methyl; $R^b$ is hydro, methyl, ethyl, trifluoromethyl, phenyl, pyridyl, naphthyl, thiophenyl, furyl, thienyl, cyclopentyl, or pentyl; $R^c$ is hydro or trifluoromethyl; or $R^a$ and $R^c$ are taken together with the carbons to which they are attached to form a cyclohexenyl ring; $R^d$ is hydro, methyl, or $CH_2CF_3$; and n is 0 or 1.

In these embodiments, the aryl or heteroaryl rings optionally are substituted with one or more of nitro, amino, methoxy, trifluoromethyl, fluoro, chloro, methyl, phenyl, hydroxy, $NHSO_2$aryl, $OSi(C_{1-4}alkyl)_3$, or OC(=O)tbutyl.

In most preferred embodiments, $R^3$ is hydro or phenyl; $R^2$ is benzyl, hydro, isopropyl, phenyl, or methyl; and $R^1$ is —C(=O)CH=CHCH_3,

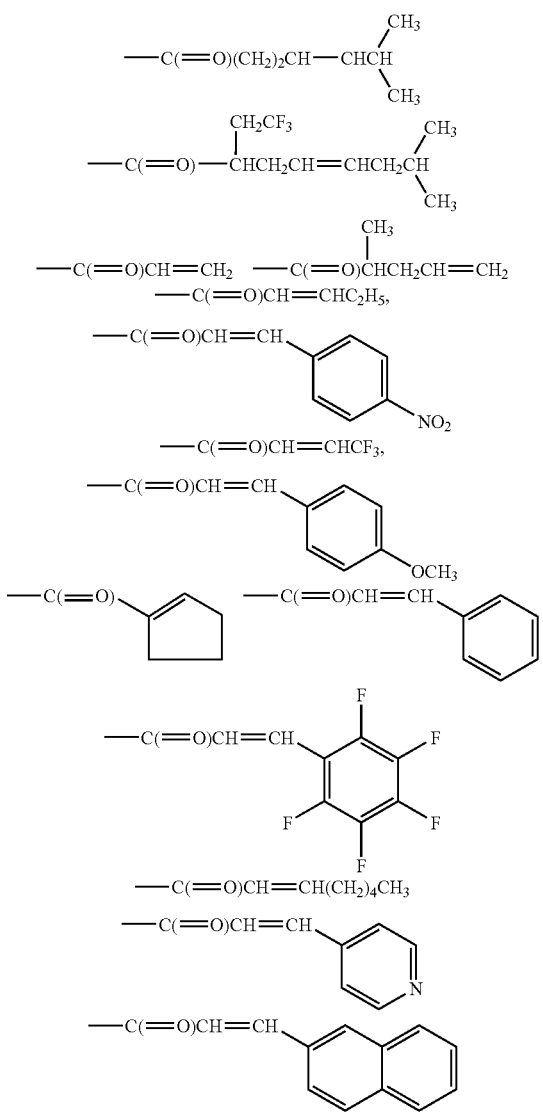

-continued
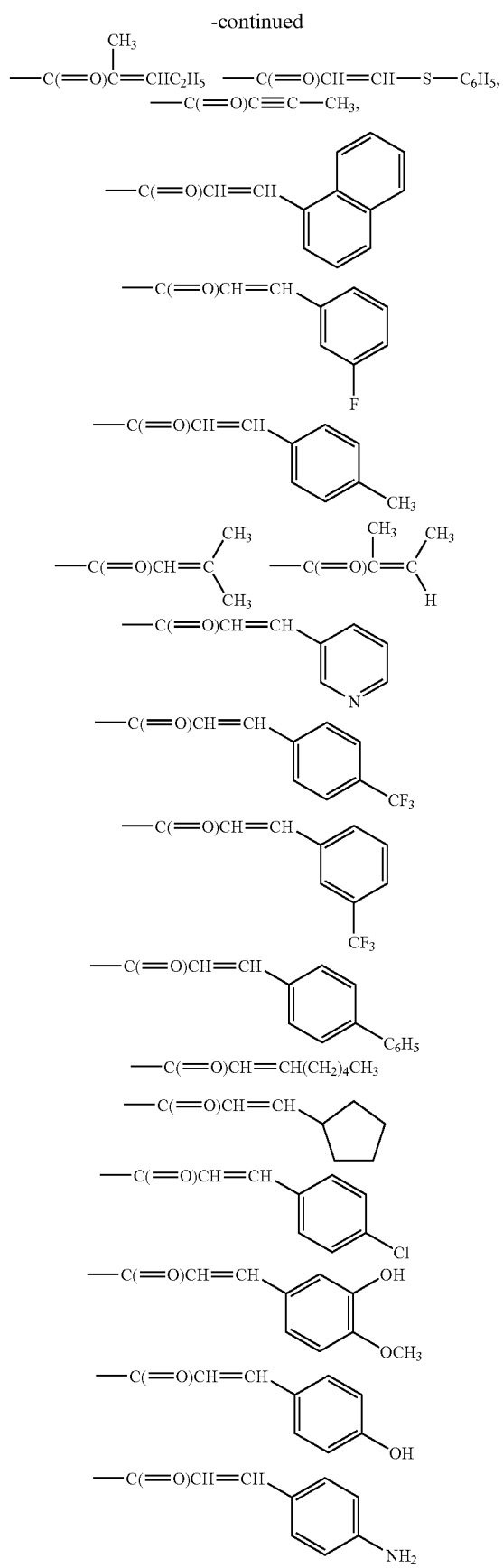
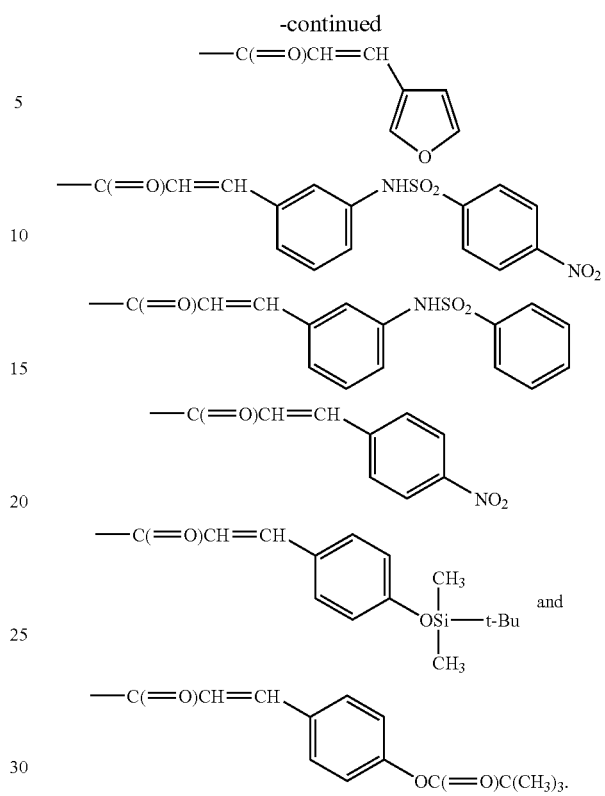
The aryl and heteroaryl substituents present on compounds of the present invention can be unsubstituted or substituted groups selected form the group consisting of
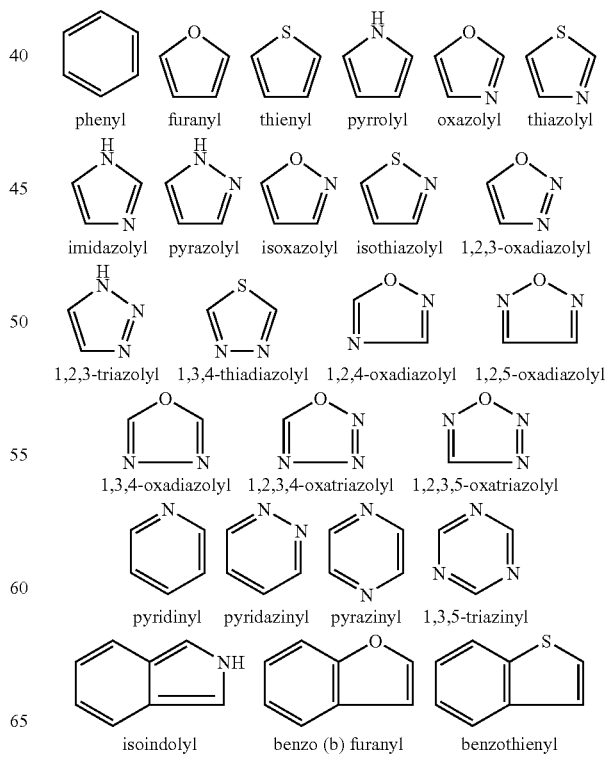

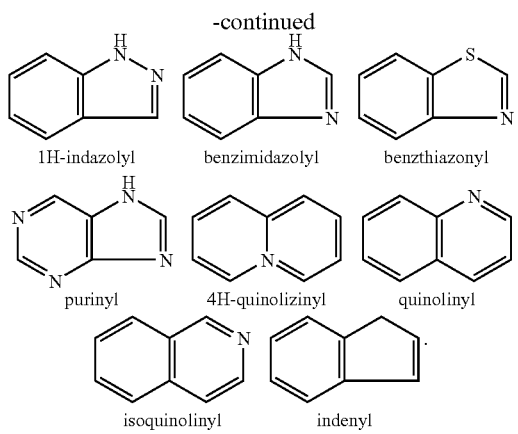

1H-indazolyl   benzimidazolyl   benzthiazonyl purinyl   4H-quinolizinyl   quinolinyl isoquinolinyl   indenyl Compounds of the present invention can contain one or more asymmetric center, and, therefore, can exist as stereoisomers. The present invention includes both racemic mixtures and individual stereoisomers of the compounds of the present invention.

Pharmaceutically acceptable salts of compounds of the present invention can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the present invention also can provide pharmaceutically acceptable metal salts, in particular alkali metal salts and alkaline earth metal salts, with bases. Examples include the sodium, potassium, magnesium, and calcium salts.

Compounds of the present invention are potent inhibitors of cell motility and cell growth. Thus, compounds of the present invention are of interest for use in therapy, specifically for the treatment of a variety of conditions where inhibition of cell motility and growth is considered to be beneficial.

Cell motility and cell growth are particularly attractive targets for inhibition because an inhibitor of cell motility and growth provides effects which are beneficial in the treatment of various disease states. The biochemical, physiological, and clinical effects of cell motility and cell growth inhibitors therefore suggest their utility in a variety of cancers by targeting various control points in cancer progression, including angiogenesis and metastasis. The compounds of the present invention, therefore, are useful in treating various cancers, while minimizing or eliminating adverse side effects due to the reversible nature of the inhibitory effect.

An especially important use of the compounds of the present invention is the treatment of a cancer. Thus, the present invention is directed to the use of compounds of the present invention, a pharmaceutically acceptable salt, prodrug, or solvate thereof, or a pharmaceutical composition containing any of these entities, for the manufacture of a medicament for the curative or prophylactic treatment of a cancer in a mammal, including humans.

As used above and hereafter, the term "treatment" includes preventing, lowering, stopping, or reversing the progression or severity of the condition or symptoms being treated. As such, the term "treatment" includes both medical therapeutic and/or prophylactic administration, as appropriate, including, but not limited to, the diseases and conditions discussed above.

It also is understood that "a compound of the present invention," or a physiologically acceptable salt, prodrug, or solvate thereof, can be administered as the neat compound, or as a pharmaceutical composition containing either entity.

The present invention also is directed to a method of treating conditions and disorders wherein inhibition of cell motility and cell growth provides a benefit, in a human or nonhuman animal body, comprising administering to said body a therapeutically effective amount of a compound of the present invention. According to another aspect of the present invention, there is provided the use of a compound of formula (I) for the manufacture of a medicament for the treatment of conditions and disorders wherein inhibition of cell motility provides a benefit.

In vivo methods of treatment are specifically contemplated. Thus, for example, the present invention includes a method of treating cancer in a mammal comprising the steps of administering to the mammal (a) a compound of the present invention to inhibit cell motility and cell growth and (b) an optional second active compound or agent for effecting cancer treatment, e.g., a chemotherapeutic agent or radiation, wherein the compound or compounds are administered at concentrations effective to effect inhibition of cell growth and cell motility in the mammal. Administration to humans is specifically contemplated, but administration to other animals, including pets, livestock, zoo-specimens, wildlife, and the like, also is contemplated.

Compounds of the present invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the present invention is a preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in a sufficient amount to achieve its intended purpose. More specifically, a "therapeutically effective amount" means an amount effective to prevent development of a disease in, or to alleviate the existing symptoms of a disease in, the subject being treated. Therefore, a "therapeutically effective amount" refers to that amount of the compound that results in achieving the desired effect. Determination of a therapeutically effective amount is well within the capability of those skilled in the art, especially in light of the detailed disclosure provided herein.

The toxicity and therapeutic efficacy of compounds of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage is selected by the individual physician in view of the patient's condition. Dosage amount and interval can be adjusted individually to provide plasma levels of a compound of the present invention which are sufficient to maintain therapeutic effects. Therefore, the amount of a compound of the present invention administered is dependent on the subject being treated, including the subject's weight, the severity of the affliction, the manner of administration, and the judgment of the prescribing physician.

Specifically, for administration to a human in the curative or prophylactic treatment of the conditions and disorders identified above, dosages of a compound of the present invention generally are about 0.1 to about 1000 mg daily for an average adult patient (70 kg). Thus, for a typical adult patient, individual doses, for example, tablets or capsules, contain 0.1 to 500 mg of active compound, in a suitable pharmaceutically acceptable vehicle or carrier, for administration in single or multiple doses, once or several times per day. Dosages for intravenous, buccal, or sublingual administration typically also are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the present invention can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of the present invention into compositions that can be used pharmaceutically.

Such pharmaceutical compositions can be manufactured in a conventional manner, e.g., by conventional mixing, dissolving, granulating, dragee-making, levigating, emulsifying, encapsulating, entrapping, or lyophilizing processes. Proper formulation is related to the route of administration chosen. When a therapeutically effective amount of a compound of the present invention is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injecttion, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of the present invention with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of the present invention with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For veterinary use, a compound of the present invention or a nontoxic salt thereof, is administered as a suitably acceptable formulation in accordance with normal veterinary practice. The veterinarian readily can determine the dosing regimen and route of administration that is most appropriate for a particular animal.

Thus, the present invention provides a pharmaceutical composition comprising a compound of the present invention, together with a pharmaceutically acceptable diluent or carrier therefor. The present invention also provides a process of preparing a pharmaceutical composition comprising a compound of the present invention, which process comprises mixing a compound of the present invention, together with a pharmaceutically acceptable diluent or carrier therefor.

In a particular embodiment, the invention includes a pharmaceutical composition for the curative or prophylactic treatment of cancer and other diseases and conditions wherein inhibition of cell motility and cell growth provides a benefit in a mammal, including humans, comprising a compound of the present invention or a pharmaceutically acceptable salt thereof, together with a pharmaceutically acceptable diluent or carrier.

A composition of the present invention can be administered to an individual alone, or in concert with a second therapeutically active agent. The second therapeutically active agent is a compound useful in treating the disease or condition afflicting the individual, and for which the individual is receiving treatment with a compound of the present invention. For example, if an individual is being treated for cancer, the individual can be administered a therapeutically effective amount of a compound of the present invention and a second therapeutically active agent useful in the treatment of cancer, for example, a chemotherapeutic drug or radiation. The cell motility and cell growth inhibitor of the present invention and second therapeutically active agent can be administered either simultaneously or sequentially. If administered sequentially, either the cell motility inhibitor or second therapeutically active agent can be administered first.

Compounds of the present invention can enhance the therapeutic benefit of radiation and chemotherapy treatment, including induction chemotherapy, primary (neoadjuvant) chemotherapy, and both adjuvant radiation therapy and adjuvant chemotherapy. In addition, radiation and chemotherapy are frequently indicated as adjuvants to surgery in the treatment of cancer. The goal of radiation and chemotherapy in the adjuvant setting is to reduce the risk of recurrence and enhance disease-free survival when the primary tumor has been controlled. Chemotherapy is utilized as a treatment adjuvant for colon, lung, and breast cancer, frequently when the disease is metastatic. Adjuvant radiation therapy is indicated in several diseases including colon, lung, and breast cancers as described above. For example, radiation frequently is used both pre- and post-surgery as components of the treatment strategy for rectal carcinoma. Compounds of the present invention are particularly useful following surgery in the treatment of cancer in combination with radio- and/or chemotherapy.

Electromagnetic radiation treatment of other diseases not listed herein also is contemplated by the present invention. The terms "electromagnetic radiation" and "radiation" as used herein include, but are not limited to, radiation having the wavelength of $10^{-20}$ to 100 meters. Preferred embodiments of the present invention employ the electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Chemotherapeutic agents that can be used include, but are not limited to, alkylating agents, antimetabolites, hormones and antagonists, radioisotopes, antibodies, as well as natural products, and combinations thereof. For example, an inhibitor compound of the present invention can be administered with antibiotics, such as doxorubicin and other anthracycline analogs, nitrogen mustards, such as cyclophosphamide, pyrimidine analogs, such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modalite, e.g., surgery or radiation, also referred to 5-herein as "adjunt antineoplastic modalities." Examples of chemotherapeutic agents useful for the method of the present invention are listed in the following table.

Alkylating agents
Nitrogen mustards mechlorethamine
cyclophosphamide
ifosfamide
melphalan
chlorambucil
Nitrosoureas carmustine (BCNU)
lomustine (CCNU)
semustine (methyl-CCNU)
Ethylenimine/Methylmelamine thriethylenemelamine (TEM)
triethylene
thiophosphoramide
(thiotepa)
hexamethylmelamine
(HMM, altretamine)
Alkyl sulfonates busulfan
Triazines dacarbazine (DTIC)
Antimetabolites Folic Acid analogs
methotrexate
trimetrexate
Pyrimidine analogs
5-fluorouracil
fluorodeoxyuridine
gemcitabine
cytosine arabinoside -continued (AraC, cytarabine)
5-azacytidine
2,2'-difluorodeoxycytidine
Purine analogs
6-mercaptopurine
6-thioguanine
azathioprine
2'-deoxycoformycin
(pentostatin)
erythrohydroxynonyladenine
(EHNA)
fludarabine phosphate
2-chlorodeoxyadenosine
(cladribine, 2-CdA)
Type I Topoisomerase
Inhibitors camptothecin
topotecan
irinotecan
Natural products
Antimitotic drugs paclitaxel
vinca alkaloids
vinblastine (VLB)
vincristine
vinorelbine
Taxoterea ® (docetaxel)
estramustine
estramustine phosphate
Epipodophylotoxins etoposide
teniposide
Antibiotics actimomycin D
daunomycin
(rubidomycin)
doxorubicin
(adriamycin)
mitoxantroneidarubicin
bleomycinsplicamycin
(mithramycin)
mitomycinC
dactinomycin
Enzymes L-asparaginase
Biological response
modifiers interferon-alpha
IL-2
G-CSF
GM-CSF
Differentiation Agents retinoic acid
derivatives
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinum coordination -continued complexes cisplatin
carboplatin
Anthracenedione mitoxantrone
Substituted urea hydroxyurea
Methylhydrazine
derivatives N-methylhydrazine
(MIH)
procarbazine
Adrenocortical
suppressant mitotane (o,p'-DDD)
ainoglutethimide
Cytokines interferon (α, β, γ)
interleukin-2
Hormones and antagonists
Adrenocorticosteroids/
antagonists prednisone and equivalents
dexamethasone
ainoglutethimide
Progestins hydroxyprogesterone
caproate
medroxyprogesterone acetate
megestrol acetate
Estrogens diethylstilbestrol
ethynyl estradiol/
equivalents
Antiestrogen tamoxifen
Androgens testosterone propionate
fluoxymesterone/equivalents
Antiandrogens flutamide
gonadotropin-releasing
hormone analogs
leuprolide
Nonsteroidal antiandrogens flutamide
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines Examples of chemotherapeutic agents that are particularly useful in conjunction with radiosensitizers include, for example, adriamycin, camptothecin, carboplatin, cisplatin, daunorubicin, doxorubicin, interferon (alpha, beta, gamma), interleukin 2, irinotecan, docetaxel, paclitaxel, topotecan, and therapeutically effective analogs and derivatives of the same.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian.

Compounds of the present invention can be prepared by any suitable method known in the art, or by the following processes which form part of the present invention. In the methods below, $R^1$, $R^2$, and $R^3$, as well as $R^a$, $R^b$, $R^c$, and $R^d$, are defined above. For example, compounds of the present invention can be prepared according to the following synthetic schemes comprising converting a compound (V) to a compound (VI) by Method A or Method B.

It should be understood that protecting groups can be utilized in accordance with general principles of synthetic organic chemistry to provide compounds of the present invention. Protecting group-forming reagents, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of the present invention not specifically exemplified herein can be prepared by persons skilled in the art.

In addition, a compound of the present invention can be converted to another compound of the present invention. Thus, for example, a particular R substituent can be interconverted to prepare another suitably substituted compound of the present invention. Examples of appropriate interconversions include, but are not limited to, OR to hydroxy by suitable means (e.g., using an agent such as $BBr_3$ or a palladium catalyst, like palladium-on-carbon, with hydrogen), or amino to substituted amino, such as acylamino or sulphonylamino, using standard acylating or sulfonylating conditions.

Compounds of the present invention can be prepared by the methods above as individual stereoisomers or as a racemic mixture. Individual stereoisomers of the compounds of the invention can be prepared from racemates by resolution using methods known in the art for the separation of racemic mixtures into their constituent stereoisomers, for-example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of the present invention that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of the present invention with a suitable base. Both types of salt can be formed or interconverted using ion-exchange resin techniques. Thus, according to a further aspect of the invention, a method of preparing a compound of the present invention, or prodrug thereof, is provided, followed by (i) salt formation, or (ii) solvate (e.g., hydrate) formation.

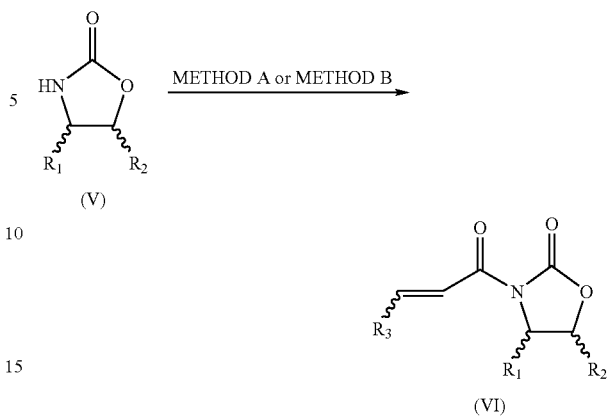

Method A

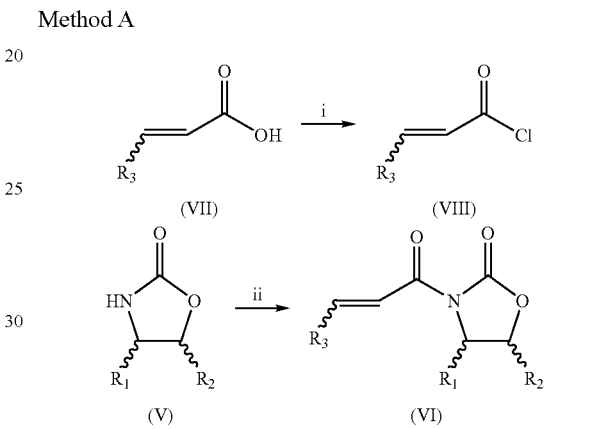

Reagents and Conditions: i) thionyl chloride $(CO(Cl)_2)$, benzene, dimethylformamide (DMF), catalyst (cat.), room temperature (rt); ii) n-butyl lithium (n-BuLi), tetrahydrofuran (THF), acid chloride (VIII), −78° C. to rt.

Method B

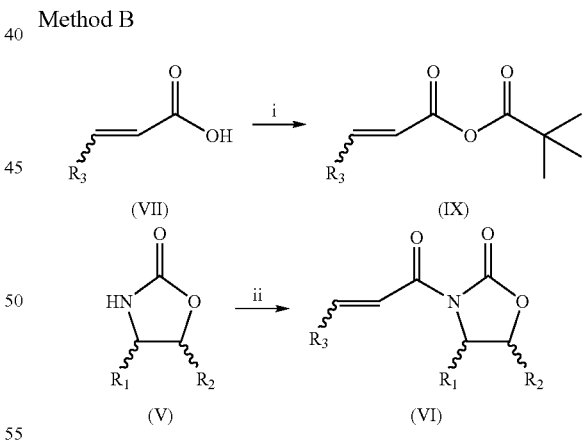

Reagents and Conditions: i) triethylamine ($Et_3N$), THF, pivaloyl chloride, −78° C. to 0° C.; ii) n-BuLi, THF, acid anhydride (IX), −78° C. to rt.

General Procedure for Method B

To a cold (−78° C.) solution of the unsaturated acid (VII) (1.1 equiv) in anhydrous THF were added pivaloyl chloride (1.1 equiv), followed by (1.2 equiv) of triethylamine. The reaction mixture was stirred at −78° C. for 30 minutes, at 0° C. for 1 hour, then recooled to −78° C. In a separate flask, n-BuLi (1.0 equiv) was added to a solution of a desired oxazolidinone (V) (1.0 equiv) in anhydrous THF at −78° C. After stirring the reaction mixture at −78° C. for 30 minutes, the mixed anhydride (IX) was added. The reaction mixture was stirred at −78° C. for 1 hour, then slowly allowed to warm to room temperature. The reaction mixture was quenched with 4 ml of saturated aqueous ammonium chloride and extracted with ethyl acetate. The combined organic phases were washed with brine and dried over anhydrous sodium sulfate (Na$_2$SO$_4$). After filtration, the solvent was removed under reduced pressure and the residue was purified by column chromatography.

The following illustrates the synthesis of a compound of the present invention, using Method A:

Compound 1

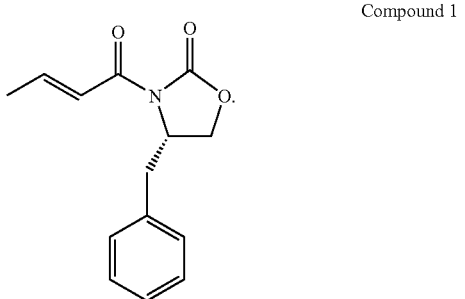

A solution of (4S)-4-benzyl-2-oxazolidinone (1.0 g, 5.6 mmol) in anhydrous THF (20 ml) was cooled to −78° C. n-BuLi (1.6 M solution in hexanes, 3.5 ml, 5.6 mmol) was added dropwise to the cooled solution. After 30 minutes, crotonyl chloride (0.59 ml, 6.2 mmol) was added to the mixture. The reaction was stirred for 30 minutes at −78° C., then warmed slowly to room temperature. The reaction mixture was quenched by addition of 4 ml saturated aqueous ammonium chloride. The resultant reaction mixture was diluted with ether, and washed with water and brine. The organic layer was dried using anhydrous Na$_2$SO$_4$ and evaporated under reduced pressure. Flash chromatography on a silica gel column using ethyl acetate/hexane (1/3) as eluent provided compound 1, i.e., (4S)-3-((E)-2-butenoyl)-4-benzyl-2-oxazolidinone, (1.50 g, 87%) as a white solid. m.p.: 83° C. IR (KBr): 3027, 2922, 2539, 1772, 1682, 1351, 1209 cm$^{-1}$. $^1$H NMR (400 MHz, CDCl$_3$): 7.36-7.15 (m, 7H, aromatic H's, CH=CH); 4.75-4.70 (m, 1H, CHN); 4.23-4.15 (m, 2H, CH$_2$O); 3.33 (dd, 1H, J=3.3, 13.4 Hz, CHHPh); 2.79 (dd, 1H, J=9.5, 13.4 Hz, CHHPh); 1.98 (dd, 3H, J=1.0, 6.2 Hz, CH$_3$). $^{13}$C NMR (100 MHz, CDCl$_3$): δ 164.69, 153.51, 146.95, 135.28, 129.37, 128.86, 127.23, 121.74, 66.01, 55.20, 37.79, 18.50.

$[\alpha]_D^{25}$=+7.77° (c 2.00, CHCl$_3$). HRMS: Calcd for C$_{14}$H$_{16}$O$_3$N (M+H)$^+$: 246.1125. Found: 246.1127.

Another compound, i.e., compound 11, having a structure:

Compound 11

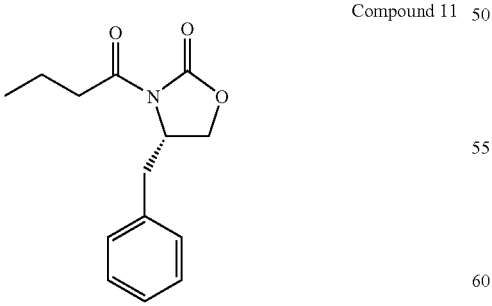

was prepared from compound 1 as follows.

10% Pd/C (0.10 g) was added to a solution of compound 1 (1.00 g, 4.08 mmol) in ethyl acetate (20.0 mL). The reaction mixture was stirred in a hydrogen atmosphere (1 atm) for 1 hour, then filtered through celite. The filtrate then was concentrated. Flash chromatography over silica gel with hexane:ethyl acetate (4:1) as eluent provided purified compound 11 (0.98 g, 97%) as a colorless oil. IR (film): 2963, 1779, 1699, 1387, 1215, 771 cm$^{-1}$; $^1$H NMR (400 MHz, CDCl$_3$) δ: 7.44-7.19 (m, 5H, Ph), 4.70-4.64 (m, 1H, CHN), 4.22-4.14 (m, 2H, CH$_2$O), 3.29 (dd, 1H, J=3.2, 13.2 Hz, CHHPh), 3.01-2.83 (m, 2H, CH$_2$CO), 2.77 (dd, 1H, J=9.6, 13.2 Hz, CHHPh), 1.77-1.68 (m, 2H, CH$_2$CH$_3$), 1.03 (t, 3H, J=7.4 Hz, CH$_3$); $^{13}$C NMR (100 MHz, CDCl$_3$) δ: 173.12, 153.38, 135.24, 129.42, 128.85, 127.23, 66.06, 55.04, 37.84, 37.29, 17.61, 13.60; $[\alpha]_D^{25}$=+71.0 (c 0.20, CHCl$_3$); HRMS calcd for C$_{14}$H$_{17}$O$_3$N (M$^+$): 247.1203; found: 247.1202.

Other compounds of the present invention, and some comparative compounds, were synthesized using these same procedures and appropriate starting materials. Additional examples of the present invention, and comparative examples, include, but are not limited to:

Compound 1

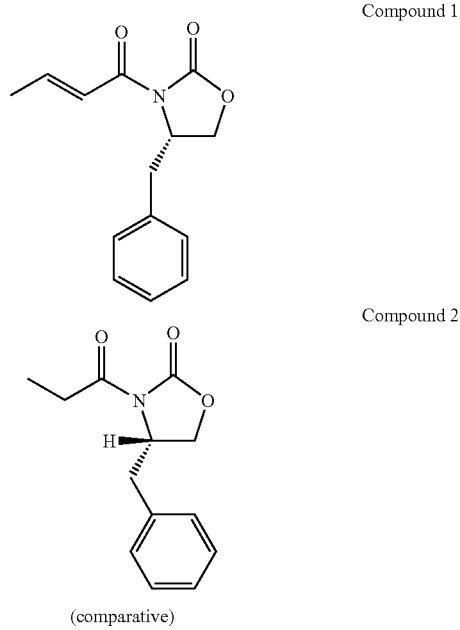

Compound 2

(comparative)

Compound 3

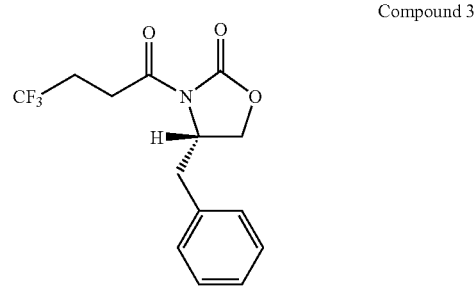

(comparative)

Compound 4

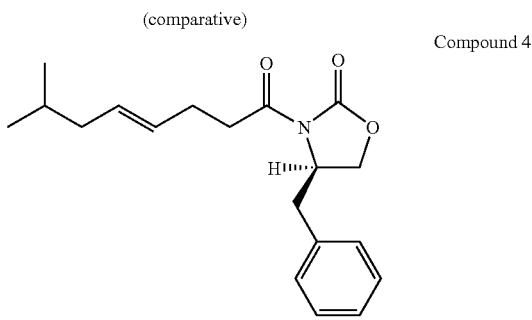

-continued
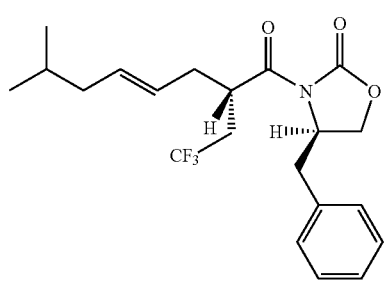
Compound 5
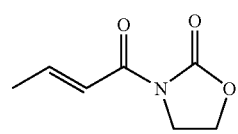
Compound 6
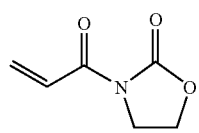
Compound 7
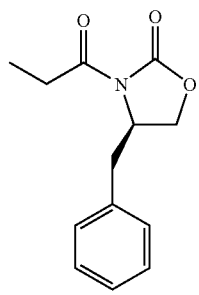
Compound 8
(comparative)
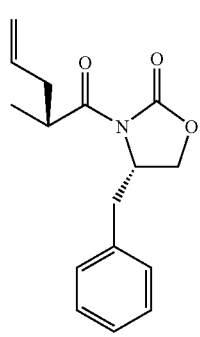
Compound 9
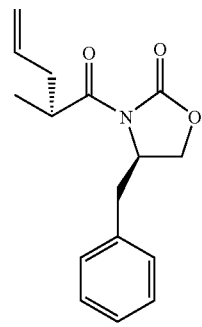
Compound 10
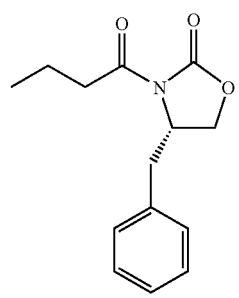
Compound 11
(comparative)
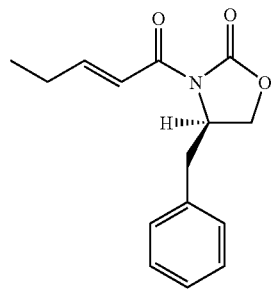
Compound 12
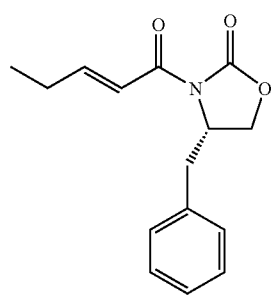
Compound 13

Compound 14
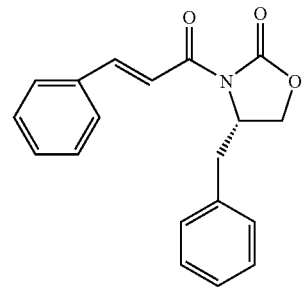
Compound 15
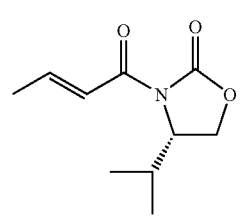
Compound 16
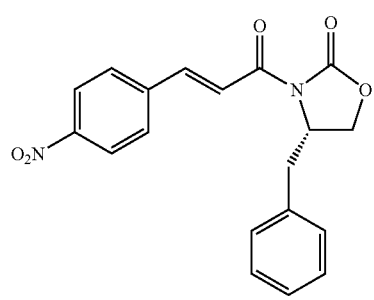
Compound 17
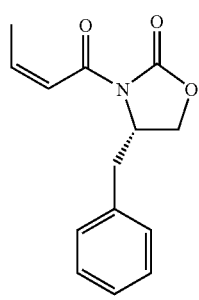
Compound 18
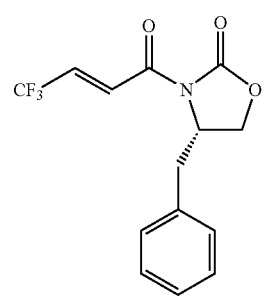
Compound 19
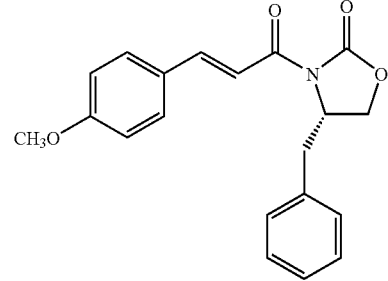
Compound 20
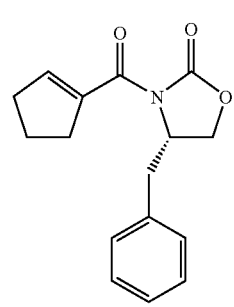
Compound 21
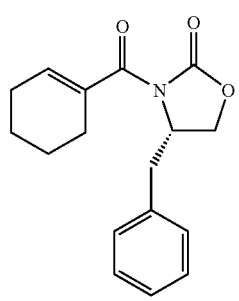
Compound 22
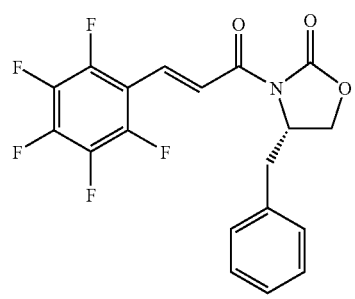
Compound 23
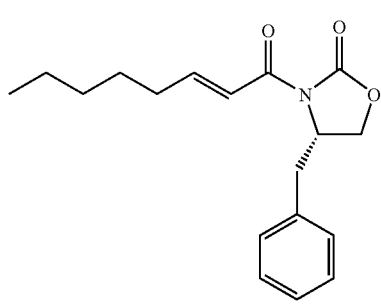

-continued
Compound 24
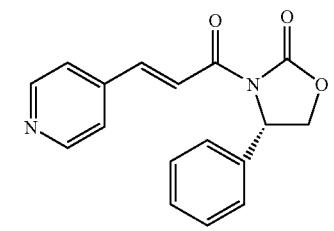
Compound 25
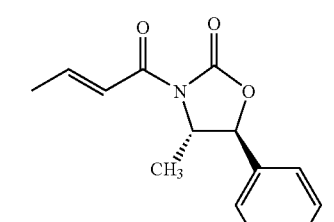
Compound 26
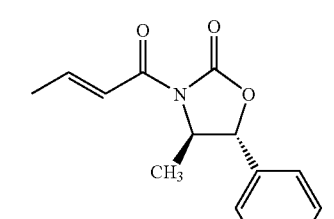
Compound 27
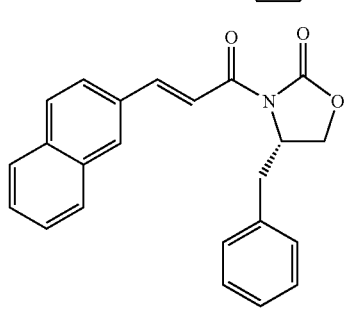
Compound 28
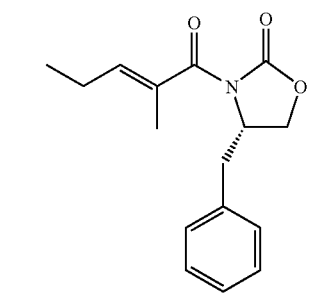
Compound 29
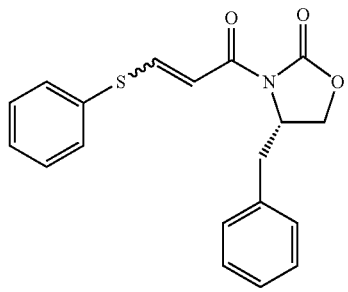
-continued
Compound 30
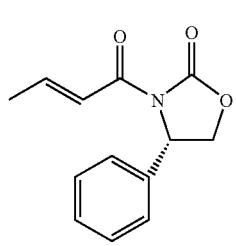
Compound 31
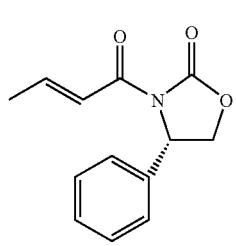
Compound 32
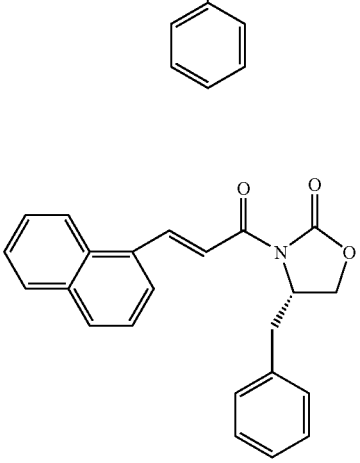
Compound 33
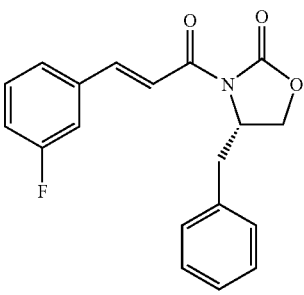
Compound 34
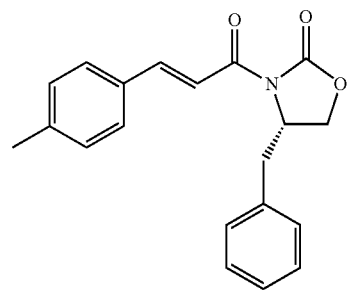

Compound 35
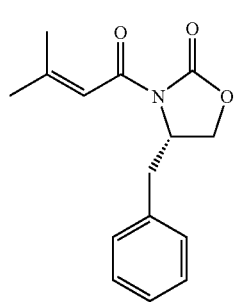
Compound 36
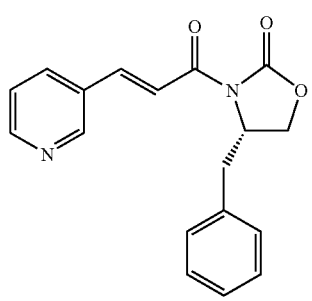
Compound 37
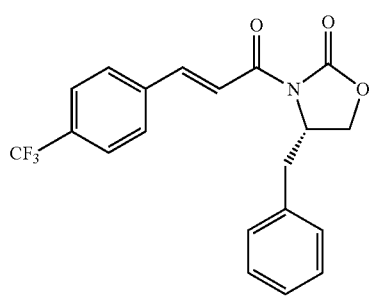
Compound 38
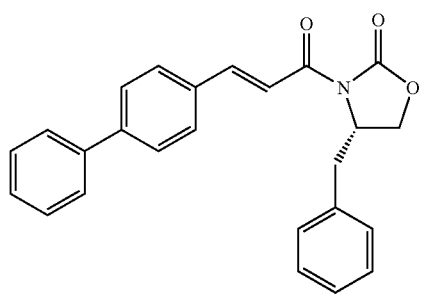
Compound 39
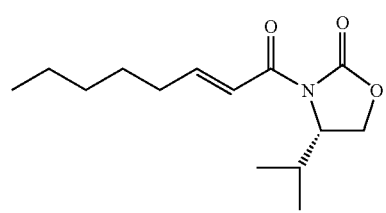
Compound 40
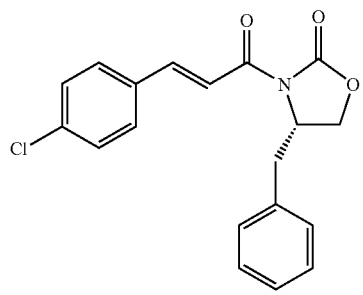
Compound 41
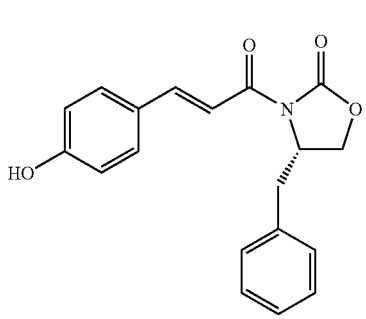
Compound 42
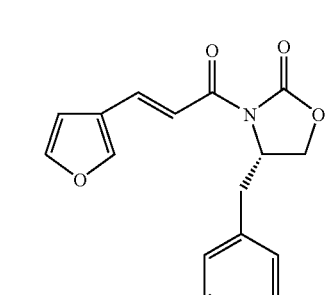
Compound 43
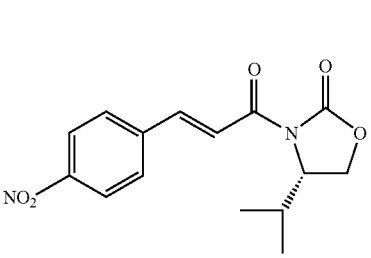
Compound 44
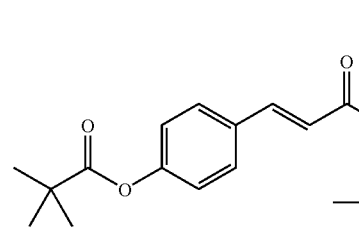

-continued
Compound 45
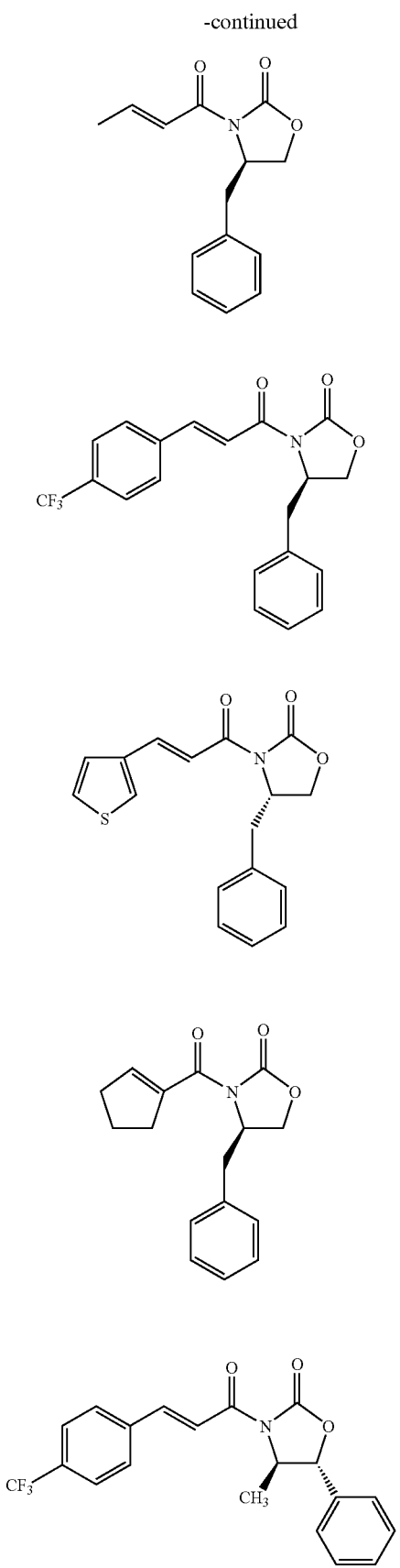
Compound 46
Compound 47
Compound 48
Compound 49
-continued
Compound 50
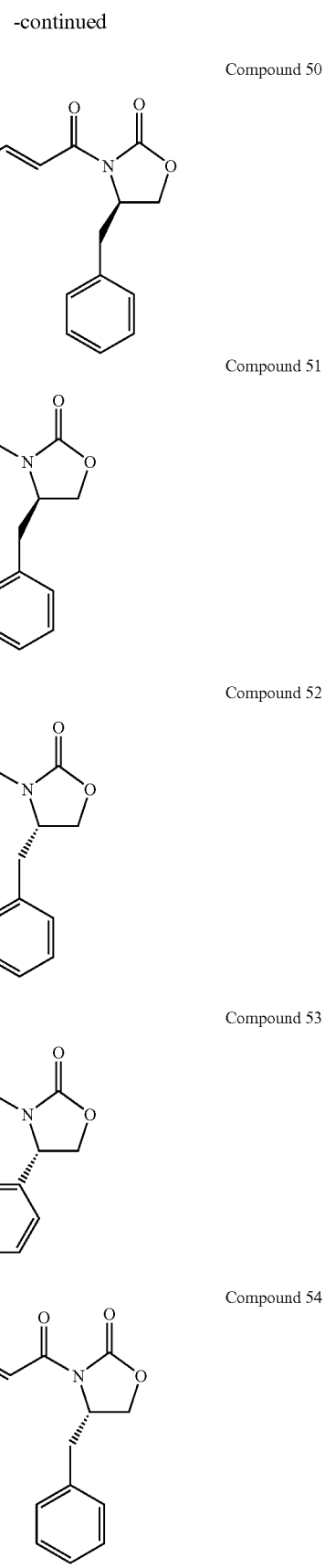
Compound 51
Compound 52
Compound 53
Compound 54

-continued
Compound 55
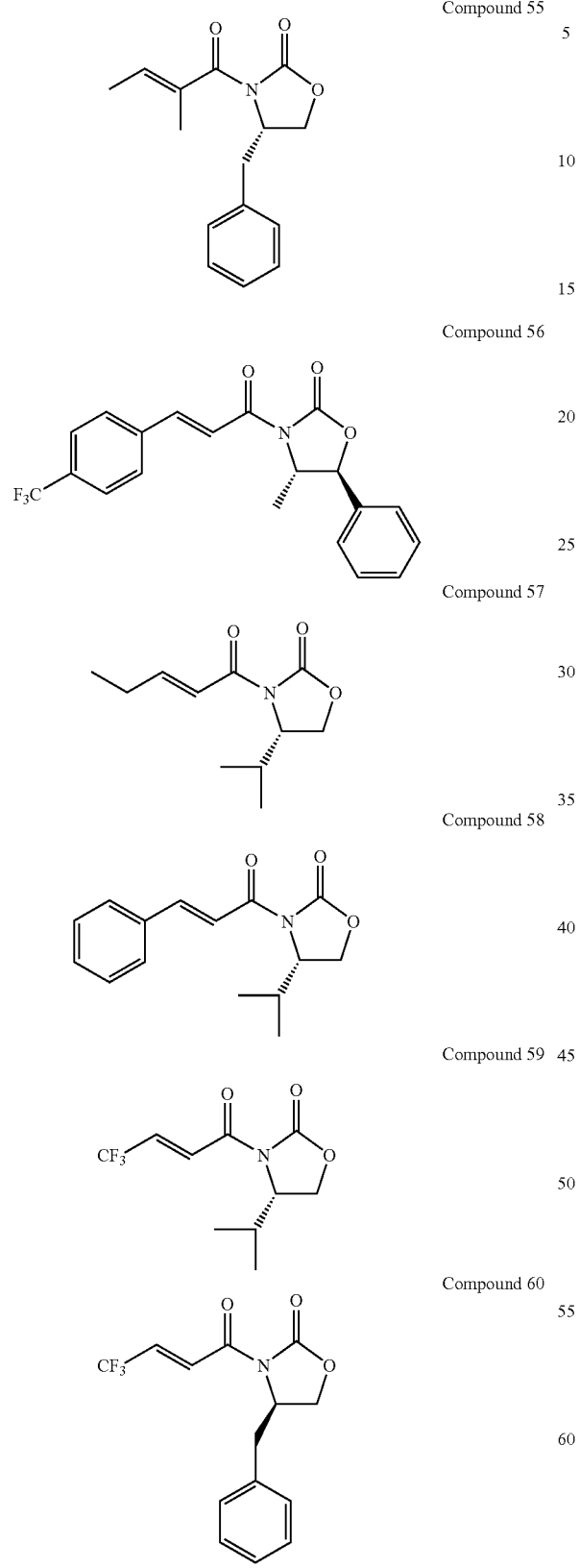
Compound 56
Compound 57
Compound 58
Compound 59
Compound 60
-continued
Compound 61
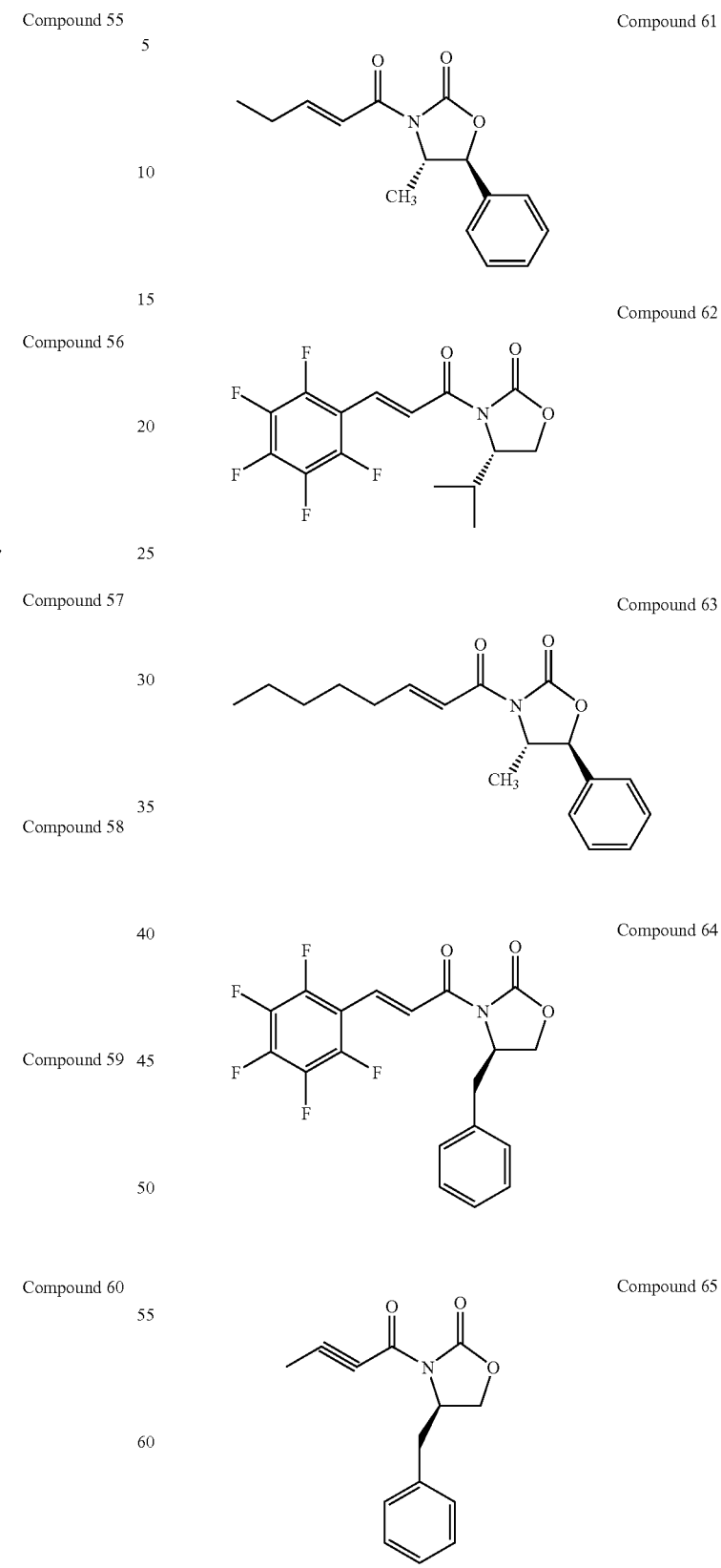
Compound 62
Compound 63
Compound 64
Compound 65

-continued

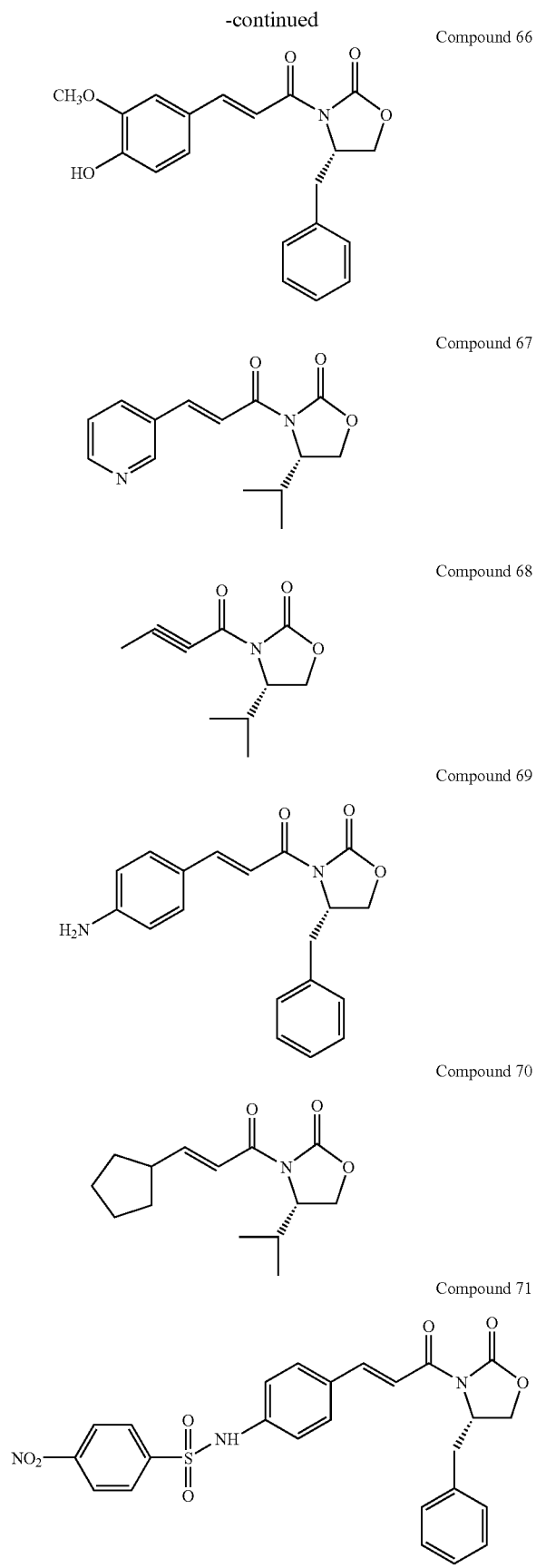

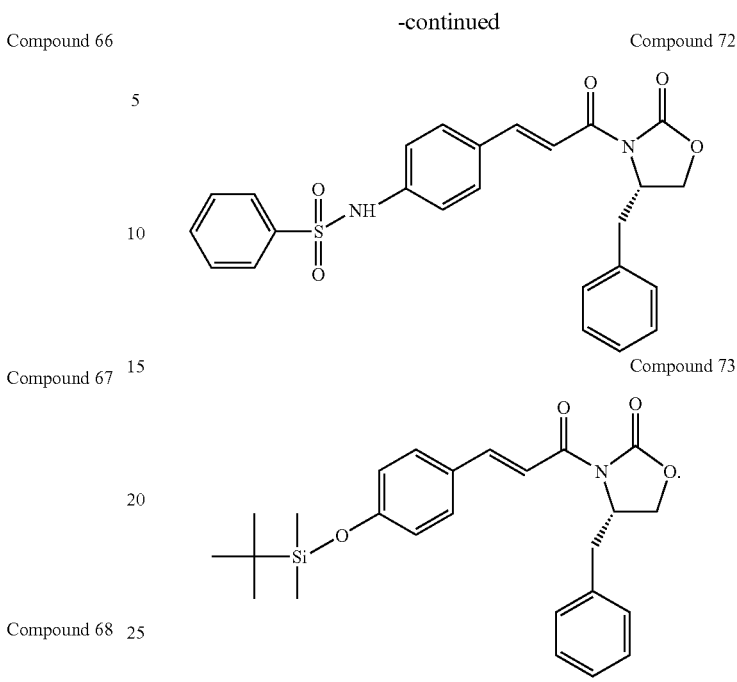

Compounds of the present invention were tested for an ability to inhibit cell motility. The ability of a compound to inhibit cell motility is related to the $IC_{50}$ value for the compound, i.e., the concentration of inhibitor required for 50% inhibition of cell motility. The $IC_{50}$ value for compounds of the present invention were determined using the procedure set forth hereafter.

The in vitro cell motility inhibitory $IC_{50}$ values of compounds set forth herein were determined by measuring the inhibition as a function of the concentration of the test compound over a range of 0 to 1 mM. The $IC_{50}$ values of the compounds of the present invention tested in the aforementioned assay ranged from about 0.01 µM to about 10 µM.

The compounds of the present invention typically exhibit a biological $IC_{50}$ value of less than about 50 µM, and preferably less than about 40 µM, and more preferably less than about 30 µM. The compounds of the present invention more preferably exhibit a biological $IC_{50}$ value of less than about 25 nM, and often less than about 20 nM. To achieve the full advantage of the present invention, a present cell motility inhibitor has an $IC_{50}$ of about 700 pM (picomolar) to about 15 µM.

A method of determining the ability of a compound to inhibit or accelerate cell motility is a scrape-wound closure assay using cultured mammalian epithelial cell monolayers. Mechanical scraping of the epithelial monolayer induces cell sheet migration into the resulting gap, a phenomenon characteristic of wounded epithelia and mechanistically related to normal epithelial movements during embryonic morphogenesis (A. Jacinto et al., *Nat. Cell Biol*, 3, E117 (2001)). Epithelial cell sheet migration in this method proceeds by a Rac- and phosphoinositide-dependent cell crawling mechanism resembling the motility of other animal cells that move as individuals rather than as cell sheets (G. Fenteany et al., *Curr. Biol.*, 10, 831 (2000)).

Wound closure in MDCK cell monolayers primarily involves cell spreading and motility rather than proliferation based on observations and treatments that block cell growth without inhibiting closure. However, after closure is complete and the gap is covered, cell division is observed in the former wound area, presumably as part of a homeostatic mechanism to regain the original cell density (M. F. Olson et al., *Science*, 269, 1270 (1995)). Wound closure involves Rac- and phosphoinositide-dependent actin polymerization and protrusion-driven cell crawling behavior, where force generation for movement is distributed from the wound margin to several rows of cells behind the margin. Accordingly, this method is excellent for determining whether a compound affects cell motility.

This test method showed that compound 1 is a potent inhibitor of cell motility. In a separate assay, it also was demonstrated that compound 1 inhibits cell proliferation. In addition, compound 1 is biologically active at concentrations at which there is no general toxicity, as determined by Trypan Blue exclusion, morphological observations, and formation of new actin bundles at the wound margin. Reversibility of the inhibitory effects of compound 1 was demonstrated by washing compound 1 from the culture medium and replacing it with untreated medium.

Compound 1, (4S)-3-((E)-2-butenoyl)-4-benzyl-2-oxazolidinone, is a 3,4-disubstituted oxazolidinone having an electrophilic $\alpha,\beta$-unsaturated N-acyl group, which is theorized as being related to inhibitory activity. Unlike the chemically distinct 3,5-disubstituted oxazolidinones, such as linezolid, compound 1, and other compounds of the present invention, do not exhibit antibacterial activity against either Gram-positive or Gram-negative bacteria. Compound 1 and other compounds of the present invention, however, are novel and unexpected inhibitors of eukaryotic cell motility and growth.

Compound 1 inhibits epithelial cell sheet migration during wound closure in Madin-Darby Canine Kidney (MDCK) cells in a statistically significant manner (p<0.05) (see FIG. 3). Based on dose-response data, the calculated $IC_{50}$ for inhibition of wound closure at 12 hours by compound 1 is 14.0 $\mu$M. This inhibitory-effect is reversible upon changing the medium to a medium free of compound 1. It was found that compound 1 does not act simply by inhibiting a serum component in the cell culture medium because compound 1 also inhibited wound closure to a similar degree relative to the control in serum-free conditions.

Figure 1B:
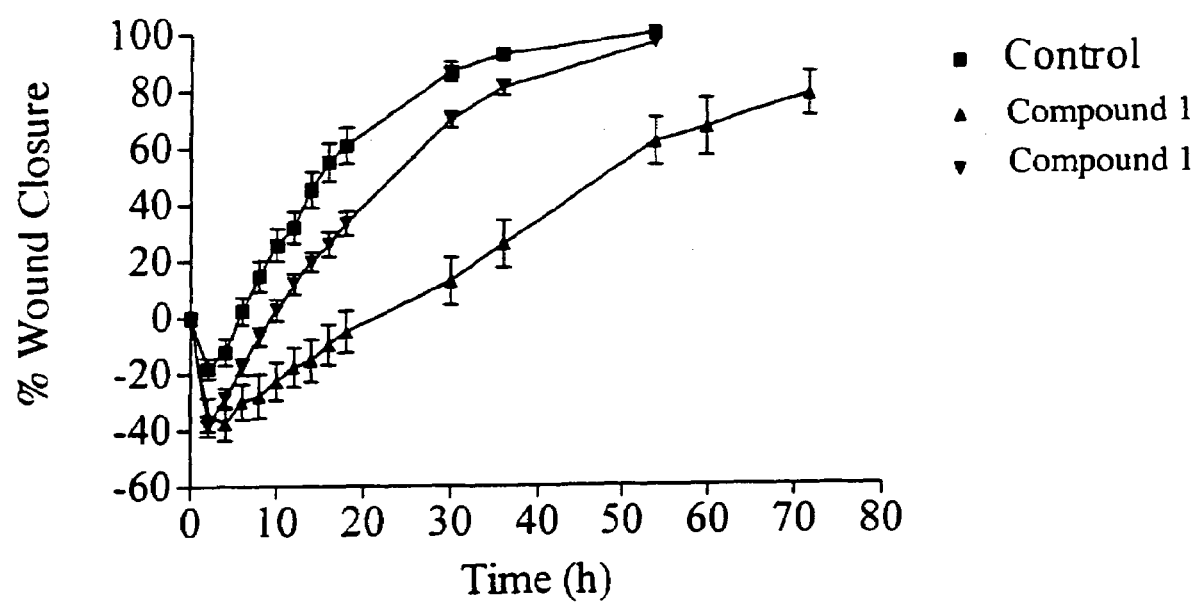
FIG. 1B contains plots of % wound closure in MDCK cell monolayers vs. time after application of a control compound (DMSO), compound 1, and compound 11.

FIGS. 1A and 1B show percent wound closure in MDCK cell monolayers in the presence or absence of compound 1 or compound 11. Values are the mean with standard error of the mean (SEM) for percent wound closure at the times indicated. FIG. 1A shows a time-course of wound closure for different concentrations of compound 1: 0.1% DMSO (control) (n=25) and 1 $\mu$M (n=9), 5 $\mu$M (n=9), 10 $\mu$M (n=15), 20 $\mu$M (n=8), 50 $\mu$M (n=19) of compound 1. The calculated $IC_{50}$ for inhibition of wound closure at 12 hours by compound 1 from the dose-response experiments was 14.0 $\mu$M (log $IC_{50}$±standard-error of log $IC_{50}$=−4.853±0.09815). FIG. 1B shows a time-course of wound closure for the following treatments: 0.1% DMSO (control, n=25 wounded cell monolayers), 50 $\mu$M compound 1 (n=19) or 50 $\mu$M compound 11 (n=10). The data presented in FIG. 1B shows statistically significant differences for percent wound closure between compound 1 (50 $\mu$M) and control (0.1% DMSO) at all time points.

It also was found that compound 1 inhibits cell motility and wound closure in Madin-Darby canine kidney (MDCK) cell monolayers, as shown by phase-contrast micrographs of cells under the following treatment conditions: (A) 0.1% (v/v) DMSO carrier control (solvent carrier control with the same final solvent concentration as in the experimental treatments) at 0, 12, and 36 hours after wounding; and (B) 50 $\mu$M compound 1 at 0, 12, and 36 hours after wounding.

Lamellipodial protrusion is known to drive most forms of animal cell crawling. At any given time in the migrating cell sheet, some cells are extending lamellipodia at the margin while others are not. Although treatment with compound 1 does not completely abolish formation of lamellipodia, treatment does result in significantly fewer cells extending lamellipodia at the margin see (Table 2), as determined by counting the number of lamellipodial protrusions at the margin and dividing by the margin perimeter length. Therefore, inhibition of cell sheet migration by compound 1 at least in part is attributed to reduced formation of lamellipodia at the would margin.

Table 1 shows that treatment with compound 1 leads to decreased formation of lamellipodial protrusions at the wound margin. Lamellipodial density at the margin of MDCK cell wounds was determined under the following treatment conditions: 0.1% DMSO (control, n=25 wounded monolayers), 50 $\mu$M compound 1 (n=19), or 50 $\mu$M compound 11 (n=10). Lamellipodial density is the number of lamellipodial protrusions detected at the wound margin until closure for the times indicated divided by margin perimeter length. Values are mean±SEM. Statistically significant differences (p<0.05) from the control value are indicated with asterisks.

TABLE 1

Lamellipodial Density vs. Time

| Time (hours) | Control | Compound 1 | Compound 11 |
|---|---|---|---|
| 2 | 0.912 ± 0.205 | 0.341 ± 0.119 | 0.563 ± 0.148 |
| 4 | 1.425 ± 0.199 | 0.573 ± 0.194* | 1.139 ± 0.270 |
| 6 | 1.592 ± 0.313 | 0.563 ± 0.142* | 1.289 ± 0.276 |
| 8 | 1.697 ± 0.244 | 0.938 ± 0.184* | 1.196 ± 0.312 |
| 10 | 1.389 ± 0.226 | 0.803 ± 0.203 | 1.609 ± 0.357 |
| 12 | 1.272 ± 0.215 | 0.520 ± 0.124* | 1.368 ± 0.309 |

The course of wound closure frequently appears biphasic. In the first few hours, there is often further gapping open of the wound as damaged, but still attached, cells at the wound margin die and perimarginal contractile actin/myosin bundles form and help establish a stable wound margin. This is followed by increasing protrusive activity at the margin and rapid closure of the wound, a process inhibited by compound 1. This inhibition is reversible upon washing compound 1 from the medium, indicating that inhibition is not secondary to an irreversible cellular process, such as apoptosis.

There is no evidence of toxicity or metabolic distress at concentrations at which compound 1 inhibits cell migration as determined by the Trypan blue exclusion cell viability assay. Cells also remain normal in morphology with both cell-substratum and cell-cell adhesion intact after treatment with compound 1. Furthermore, treatment with compound 1 does not affect formation of filamentous actin bundles at the wound margin, demonstrating that cells are still metabolically capable of forming new actin filaments, a process that requires adenosine triphosphate.

Compound 1 did not affect formation of filamentous actin bundles at wound margin as shown in fluorescence micrographs of rhodamine-phalloidin-stained MDCK cell monolayers 12 hours after wounding under the following treatment conditions: (A) 0.1% DMSO control and (B) 50 $\mu$M compound 1. Although formation of perimarginal actin bundles is not required for wound closure in this system, these actin bundles may help to distribute force in the first row of cells from actively protruding and moving cells to less-actively motile cells, thus making the closure process more regular and uniform than it would be otherwise.

Figure 2A:
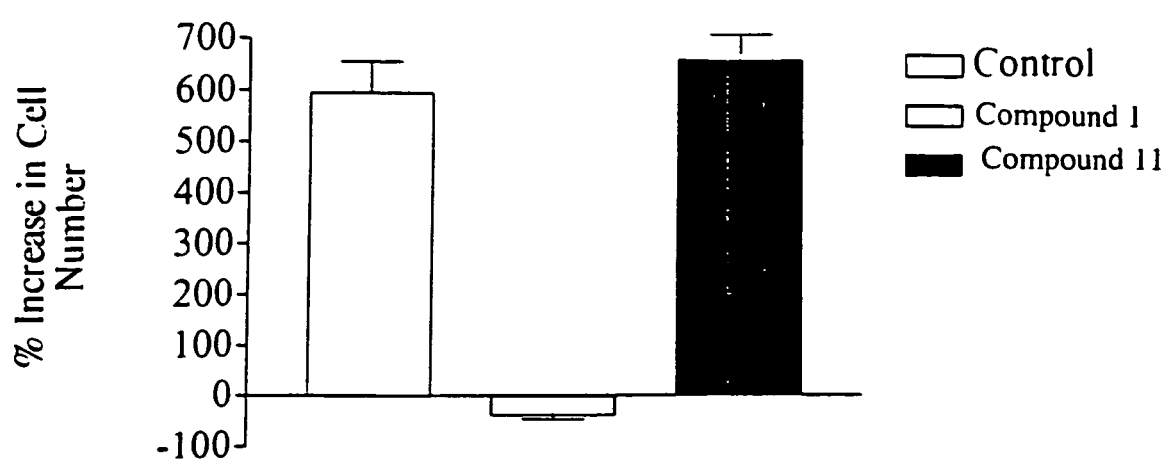
FIG. 2A contains bar graphs showing the % increase in number of MDCK cells after application of a control compound (DMSO), compound 1, and compound 11.
Figure 2B:
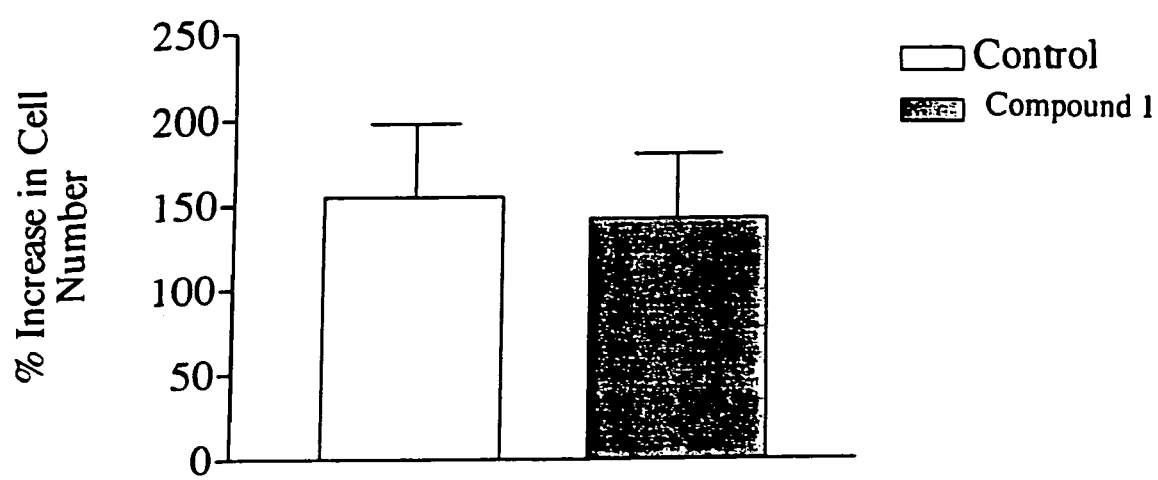
FIG. 2B contains bar graphs showing the % increase in number of MDCK cells after administration of control compound (DMSO) or compound 1, followed by rinsing of the control compound or compound 1 from the test system.

Compound 1 also inhibited cell growth in MDCK cells (FIG. 2A) at concentrations where no evidence of general toxicity exists, and in a manner that was reversed by changing the medium to a compound-free medium (FIG. 2B). FIGS. 2A and 2B show that compound 1, but not compound 11, reversibly inhibited MDCK cell proliferation. In FIG. 2A, cells were plated at low cell density ($1 \times 10^4$ cells/mL) and allowed to attach and begin to grow for 48 hours prior to the start of experiment. The treatments were 0.1% DMSO (control, n=9 cultures), 50 µM compound 1 (n=8), or 50 µM compound 11 (n=7). Reported values are mean with SEM of the percent increase in cell number from 0 to 48 hours after addition of compound 1.

FIG. 2B shows that the inhibition of cell proliferation by compound 1 was reversible by washing out the compound. The values were mean with SEM of the percent increase in cell number another 48 hours after replacement of medium containing 50 µM compound 1 (n=8 cultures) or 0.1% DMSO (n=9) with fresh medium containing 0.1% DMSO.

As discussed in detail hereafter, it also was demonstrated that compound 1 inhibited early development in frog embryos and tissue dynamics in embryonic explants with equivalent potency. The effects of compound 1 on frog embryos were most pronounced at stages after most embryonic cell proliferation occurred, when morphogenesis is mainly driven by cell motility and cell rearrangement.

Compound 1 also did not affect the growth of either Gram-positive or Gram-negative bacteria (Table 2). Furthermore, although chiral 4-substituted oxazolidinones and α,β-unsaturated N-acyloxazolidinones have become widely used in asymmetric organic-synthesis, biological activity for these oxazolidinones has not been reported (H. T. Sponsel et al., *Am. J. Physiol.*, 267, F257 (1994)). Compounds of the present invention, therefore, represents a novel class of bioactive oxazolidinone.

Table 2 shows that compound 1 does not inhibit the growth of either Staphylococcus aureus (i.e., a Gram-positive bacterial species) or *Escherichia coli* (i.e., a Gram-negative bacterial species) in the presence of 0.1% DMSO (carrier solvent control) or compound 1 (50 µM), measured as absorbance at 600 nm. Reported values are the mean ±SEM for triplicate samples.

TABLE 2

| Time (hours) | Staphylococcus aureus Control | Staphylococcus aureus Compound 1 | Escherischia coli Control | Escherischia coli Compound 1 |
|---|---|---|---|---|
| 0 | 0.091 ± 0.002 | 0.117 ± 0.037 | 0.128 ± 0.004 | 0.119 ± 0.001 |
| 1 | 0.109 ± 0.012 | 0.160 ± 0.056 | 0.190 ± 0.004 | 0.215 ± 0.005 |
| 2 | 0.259 ± 0.024 | 0.332 ± 0.130 | 0.572 ± 0.009 | 0.628 ± 0.024 |
| 3 | 0.753 ± 0.038 | 0.615 ± 0.162 | 1.137 ± 0.018 | 1.127 ± 0.019 |
| 4 | 1.394 ± 0.060 | 0.937 ± 0.181 | 1.614 ± 0.017 | 1.613 ± 0.035 |
| 17 | | | 2.725 ± 0.008 | 2.595 ± 0.024 |
| 27 | 3.695 ± 0.410 | 3.265 ± 0.196 | | |
| 31 | 4.067 ± 0.467 | 3.608 ± 0.271 | | |
| 38 | | | 2.854 ± 0.023 | 2.795 ± 0.050 |

It is theorized, but not relied upon herein, that in some embodiments, the α,β-unsaturated acyl moiety on nitrogen atom of the oxazolidinone ring of compound 1 is a reactive electrophile. Compound 1, therefore, has the potential to form a covalent complex with a nucleophilic cellular target by 1,4-addition of the nucleophile to the α,β-unsaturated acyl group. Consistent with this theory, the closest saturated analog to compound 1, i.e., compound 11, displays no statistically significant bioactivity in either wound closure or cell proliferation assays, even at the highest concenraion tested (500 µM). Compound 11 is the product of reductive hydrogenation of compound 1, and is identical in structure to compound 1 except that compound 11 lacks the C—C double bond, therefore making it chemically unreactive to a nucleohile.

However, an interaction based on addition of a nucleophilic target to the compound would be covalent and probably stable, but the effects of compound 1 in both wound closure and cell proliferation assays is reversible. An alternative theory, therefore, is that the interaction can be labile and reversible. The immediate target can be hypothesized as an endogenous nucleophilic molecule, such as glutathione, or an intracellular metabolite as opposed to a macromolecule, resulting in a conjugate, which then mediates the biological effects of treatment, presumably by interaction with a protein or other biological macromolecule. Another hypothesis is that the α,β-unsaturated N-acyl group of compound 1 may be important for a reason unrelated to its potential reactivity, such as reduced conformational flexibility.

Additional tests illustrating inhibition of cell motility and cell growth provided by compounds of the present invention, were performed on frog embryos. In particular, cell behavior and movements that underlie many aspects of gastrulation, neurulation, and body axis formation have been extensively characterized in the frog embryo (R. Keller et al., *Philos. Trans. R. Soc. Lond. B Biol. Sci.*, 355, 397-922 (2000)). *Xenopus laevis* (African clawed frog) is an established model organism in developmental biology having unique advantages in studies of vertebrate morphogenesis, such as extremely well-characterized embryology, availability of a wide range of explant and transplant techniques and manipulations, an extensive fate mapping of the embryo, and a relative ease with which direct observations of cell behavior can be made.

*Xenopus laevis* has large eggs (e.g., 1.2 mm diameter) and early embryos that develop externally in an aqueous environment, making the species useful for both embryological analysis and delivery of pharmacological agents with precise temporal control. Furthermore, *Xenopus laevis* oocytes, extracts, and embryos are well-suited for biochemical analysis and have been used extensively to isolate proteins, characterize protein function, and study the biochemistry of the cell cycle and other cellular processes.

In order to identify compounds that specifically perturb morphogenesis in the frog embryo, a suitable method for scoring embryos by characteristic defects was developed. A useful starting point was the "dorso-anterior index" (DAI). The DAI originally was constructed by adding new morphological characteristics to the older "index of axis deficiency" (S. R. Scharf et al., *Dev. Biol.*, 99, 75-87 (1983)). The DAI is a scale of dorsoanterior development wherein embryos are assigned a score based on degree of dorsoanterior phenotype (K. R. Kao et al., *Dev. Biol.*, 127, 64-77 (1988)). The scale encompasses a score of 0 (for the most axis-deficient or ventralized embryos) to 10 (for embryos with the most enhanced dorsoanterior structures), with a score of 5 signifying a normal embryo.

Because the DAI focuses only on dorsoanterior phenotypes, other categories were added to describe possible defects more comprehensively, with an emphasis on characteristics that are easily and unambiguously recognized in intact embryos, and that are diagnostic of possible effects on morphogenesis during gastrulation and neurulation. The most useful and readily scored categories that covered the most frequent deficiencies were: reduced anterior structures and microcephaly, delayed appearance or absence of eye pigmentation, overall shortness along the anteroposterior axis, bent axis, bent tail only, reduced posterior structures/tail, malformed or reduced fins, delayed or failed neural tube closure (neural fold fusion), abnormal pigmentation pattern, ventral swelling (edema), and delayed or abnormal visceral organogenesis and yolk resorption. In addition, blastopore closure, an earlier process that marks the completion of gastrulation, was observed.

In these tests, test compounds were added individually to wells each containing 4-8 embryos in 12-well plates. Embryos at stage 8.5-9, according to the classification of Nieuwkoop and Faber (P. I. Nieuwkoop et al., Normal Table of *Xenopus laevis* (Daudin). Amsterdam: North-Holland Publ.) (1967)), were used because these are late blastula stages before gastrulation begins at stage 10, which allowed focusing primarily on compounds that affect morphogenetic events in gastrulation and neurulation. These embryos, therefore, have undergone a midblastula transition at stage 8 (cleavage division 12) when zygotic transcription begins (J. Newport et al., *Cell*, 30, 675-686 (1982); J. Newport et al., *Cell*, 30, 687-696 (1982)) but have not yet started the morphogenetic movements of gastrulation. In separate experiments, as indicated in the figures, a test compound was added to embryos at the 2-cell stage (after the first cleavage division, Nieuwkoop and Faber stage 2) in order to evaluate whether additional effects were observed with earlier treatment, for example, defects due to inhibition of inductive events at the earlier stages.

This test led to the discovery that compounds of the present invention are inhibitors of morphogenesis in the frog embryo. The structures of the compounds used in the study are summarized in Table 3.

TABLE 3

Structures of N-Acyloxazolidinones
Bn = benzyl, i-Pr = isopropyl, Me = methyl, Ph = phenyl

| Compound | $R^1$ | $R^2$ | $R^5$ | $R^4$ | $R^3$ |
|---|---|---|---|---|---|
| 1 | | H | Bn | H | H |
| 6 | | H | H | H | H |
| 11 | | H | Bn | H | H |
| 13 | | H | Bn | H | H |

TABLE 3-continued

Structures of N-Acyloxazolidinones
Bn = benzyl, i-Pr = isopropyl, Me = methyl, Ph = phenyl

| Compound | $R^1$ | $R^2$ | $R^5$ | $R^4$ | $R^3$ |
|---|---|---|---|---|---|
| 15 | | H | i-Pr | H | H |
| 17 | | H | Bn | H | H |
| 23 | | H | Bn | H | H |
| 25 | | H | Me | H | Ph |
| 26 | | Me | H | Ph | H |
| 30 | | H | Ph | H | H |
| 31 | | H | Bn | H | H |
| 33 | | H | Bn | H | H |
| 35 | | H | Bn | H | H |
| 41 | | H | Bn | H | H |
| 45 | | Bn | H | H | H |

TABLE 3-continued

Structures of N-Acyloxazolidinones
Bn = benzyl, i-Pr = isopropyl, Me = methyl, Ph = phenyl

| Compound | $R^1$ | $R^2$ | $R^5$ | $R^4$ | $R^3$ |
| --- | --- | --- | --- | --- | --- |
| 52 | CH$_2$=CH–C(=O)–CH(–)– (vinyl ketone) | H | Bn | H | H |
| 54 | 3-(CF$_3$)-C$_6$H$_4$–CH=CH–C(=O)–CH(–)– | H | Bn | H | H |
| 55 | (CH$_3$)CH=C(CH$_3$)–C(=O)–CH(–)– | H | Bn | H | H |

Figure 3A:
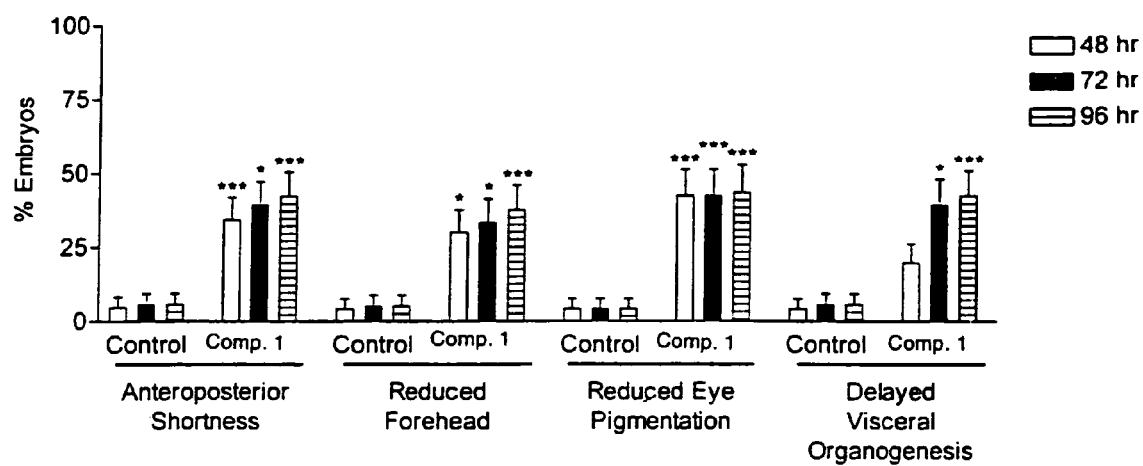
FIGS. 3A and 3B contain bar graphs showing developmental defects in embryos treated with a control compound (DMSO) or compound 1 over a 48- to 96-hour time period.

Of the characteristics evaluated, anteroposterior length, head development, eye pigmentation, visceral organogenesis, and yolk resorption were significantly different by Student's t-test in embryos treated with compound 1 at stage 8.5-9 from the control embryos, as observed later in post-neurula embryos at 48, 72, or 96 hours after treatment (FIG. 3A). FIG. 3 shows that treatment with compound 1 results in specific developmental defects.

Figure 3B:
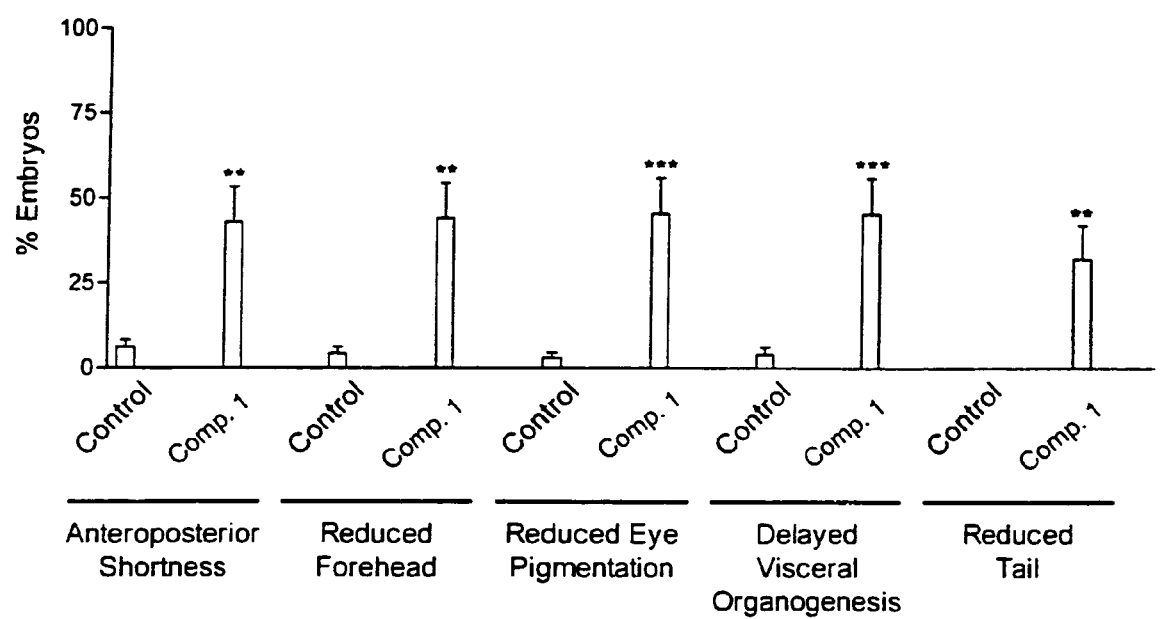

In FIGS. 3A and 3B, significance by Student's t-tests (individual experimental vs. control) was indicated as follows: *$0.01 \leq p < 0.05$; $0.001 \leq p < 0.01$; *$p < 0.001$. Each experiment was conducted in triplicate on at least three separate occasions in 12-well plates for a total of 9 or more wells per treatment (with 4-8 embryos for each well). Reported values were expressed as the mean and standard error of the mean (SEM). FIG. 3A illustrates the percentage of embryos with specific defects 48 hours (white bar), 72 hours (black bar) and 96 hours (striped bar) after addition of compound 1 to embryos at stage 8.5-9 for n=101 embryos (0.1% DMSO control) and n=129 embryos (15 µM compound 1).

The $EC_{50}$ of compound 1 with respect to the defective phenotype at 72 hours after treatment is 13.9 µM (log $EC_{50}$+ standard error of log $EC_{50}$=−4.858+0.01959, Table 2), based on dose-response data using five different concentrations over the range of the response. This value is equivalent to the compound's $IC_{50}$ for inhibition of cell migration in a mammalian epithelial cell culture model. The compound 1-treated defective embryos were alive over the course of the experiment with a functioning muscularture and nervous system based on apparently normal movement of the embryos. However, compound 1 became lethal to the embryos at concentrations above 2 to 3 times the $EC_{50}$.

Compound 1-treated embryos were markedly shorter from head to tail than control embryos at every time point, indicating an inhibitory effect on anteroposterior elongation. Development of the head was delayed, with significant frequencies of a reduced forehead (slightly microcephalic) phenotype observed in compound-treated embryos. The eye anlage formed later with compound 1 treatment, and eyes were subsequently less pigmented at every stage over the course of their development. Visceral organogenesis and accompanying yolk resorption were inhibited in treated embryos compared to control embryos. Most easily observed was the delay in formation of the gastrointestinal tract. The anal canal was significantly under-developed in compound 1-treated embryos but clearly defined in the control embryos at 96 hours.

Treatment of embryos at the 2-cell stage with compound 1 also had significant effects on anteroposterior elongation, head and eye development, visceral organogenesis, and yolk resorption (FIG. 3B). FIG. 3B shows percentage of embryos with specific defects at 48 hours after addition of compound 1 to the embryos at the 2-cell stage (after the first cleavage division, Nieuwkoop and Faber stage 2) for n=171 (0.1% DMSO control) and 98 (15 µM compound 1). In addition, reduction in the length of the tail was evident with treatment at the 2-cell stage (FIG. 3B), but not when compound 1 was added to stage 8.5-9 embryos. Therefore, the effects of compound 1 on anteroposterior elongation, head and eye development, visceral organogenesis, and yolk resorption are mediated primarily by a post-blastula activity, whereas reduction in the tail is due exclusively to a pre-gastrula activity.

Figure 4A:
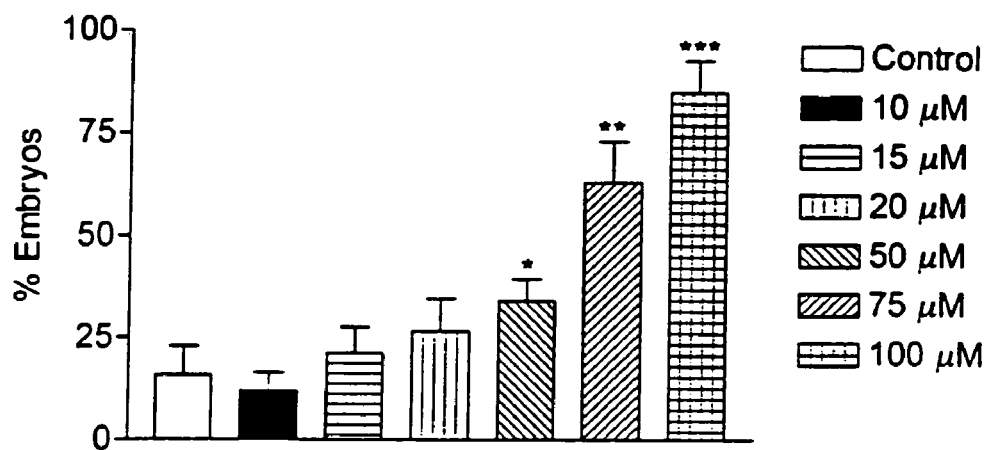
FIGS. 4A and 4B contain bar graphs showing a delay in blastopore closure arising from treatment with a control compound (DMSO) and with various concentrations of compound 1.
Figure 4B:
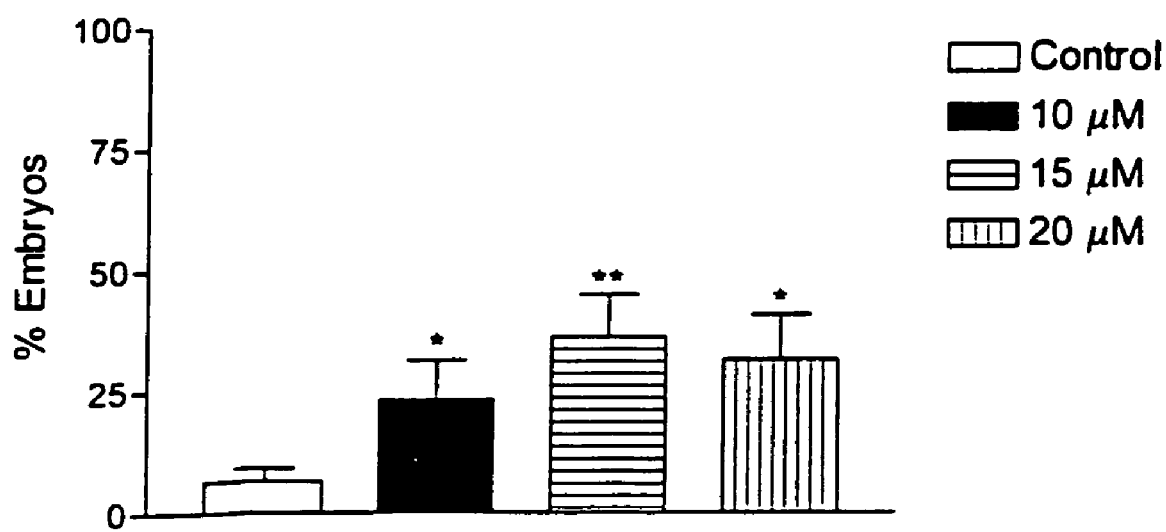

In addition to the defects observed in post-neurula embryos, blastopore closure was delayed in gastrulating embryos following compound 1 treatment at either stage 8.5-9 (FIG. 4A) or the 2-cell stage (FIG. 4B). FIG. 4 shows that treatment with compound 1 results in delayed blastopore closure.

FIG. 4A shows the percentage of embryos (mean and SEM) with open blastopore 12 hours after addition of compound 1 to embryos at stage 8.5-9 for n=101 (0.1% DMSO control), 123 (10 µM compound 1), 129 (15 µM compound 1), 119 (20 µM compound 1), 45 (50 µM compound 1), 46 (75 µM compound 1), and 50 (100 µM compound 1).

FIG. 4B shows the percentage of embryos (mean and SEM) with an open blastopore 24 hours after addition of compound to embryos at the 2-cell stage- for n=171 (0.1% DMSO control), 87 (10 µM compound 1), 84 (15 µM compound 1), and 97 (20 µM compound 1).

Blastopore closure marks the completion of gastrulation at the end of stage 12, and is the result of the tissue movements of convergent extension (R. Keller et al., *Development*, 103, 193-209 (1988)), which involves tissue narrowing (convergence) coupled with tissue elongation (extension).

Morphogenesis during gastrulation and neurulation occurs largely by cell movements and rearrangements. There is reduced cell division and increased cell motility after the midblastula transition at stage 8 in the frog embryo (J. Newport et al., *Cell*, 30, 675-686 (1982); L. D. Etkin, *Dev. Biol.*, 5, 509-225 (1988)). At gastrulation in *Xenopus laevis*, which begins at stage 10, cells at the dorsal lip of the presumptive blastopore begin to invaginate by an apical actin/myosin-dependent contraction, becoming bottle shaped (J. Hardin et al., *Development*, 103, 211-230 (1988)). The subsequent involution of tissue rolling over the blastopore lip to form the primary germ layers is mainly the result of convergent extension, a process driven by protrusive cell motility and intercalation in prospective mesodermal and neural tissues (R. Keller et al., *Philos. Trans. R. Soc. Lond. B Biol. Sci.*, 355, 897-922 (2000)). Convergent extension continues through neurulation, underlying the elongation of the anteroposterior axis that turns a spherical embryo into a cigar-shaped post-neurula embryo. These movements, therefore, are responsible for establishing much of the body plan of the organism, establishing its three-dimensional organization and positioning tissues such that they are properly oriented relative to one another, allowing appropriate inductive, and physical interactions required for later organ development to take place.

It is hypothesized, but not relied upon herein, that the effects of compound 1 are mediated by an activity or activities after stage 9 during gastrulation and neurulation, and its effects on blastopore closure and anteroposterior elongation are consistent with inhibition of convergent extension. In fact, compound 1 inhibits convergent extension in Keller sandwich explants. It is noteworthy that compound 1 also inhibits migration of mammalian epithelial cells in culture, and a similar activity in the frog embryo can account for many effects of compound 1 on development. Therefore, compound 1 affects cell motility, cell polarity, and/or cell adhesion in the embryo.

In order to determine the time following exposure to compound 1 before which its activity becomes irreversible (at which time the embryo would be committed to a defective phenotype), stage 8.5-9 embryos were treated with compound 1, then compound 1 was completely washed out at intervals of 3 hours from different parallel samples by replacing the medium with a compound-free medium. Defects were scored and tested results by Student's t-test against those for parallel control embryos, wherein DMSO carrier solvent was initially added to a final concentration of 0.1% (v/v) and then washed out at the same times as the experimental embryos. Exposure of stage 8.5-9 embryos to 15 µM compound 1 for up to 9 hours before washing out compound 1 had no significant effect on later development. However, a 12-hour or more exposure to compound 1 resulted in significant defects later in the postneurula analyses.

In an analogous experiment, when compound 1 was added to two-cell stage embryos and then washed out every hour from different parallel samples, the effects became irreversible between only 2 and 3 hours of treatment. These results indicate that between 9 and 12 hours following treatment of late blastula embryos and between 2 and 3 hours following treatment of two-cell stage embryos with compound 1, the embryos become irreversibly committed to the defective phenotype.

Dose-response experiments were conducted to calculate the $EC_{50}$ values of the different compounds of the present invention with respect to the defective phenotype (Table 4). Although defective, the treated embryos were alive with a functioning musculature and nervous system. However, at concentrations greater than 2-3 times the $EC_{50}$, the compounds became lethal to the embryos.

TABLE 4

$EC_{50}$ Values of Various N-Acyloxazolidinones
$EC_{50}$ values of each compound with respect to the defective phenotype at 72 hr following treatment, calculated from dose-response data using 5 different concentrations (with $n \geq 36$ embryos for each concentration). NA = no statistically significant biological activity at any concentration.

| Compound | $EC_{50}$ (µM) |
|---|---|
| 1 | 13.9 |
| 6 | 39.1 |
| 11 | NA |
| 13 | 54.6 |
| 15 | 25.9 |
| 17 | 19.1 |
| 23 | 58.1 |
| 25 | 13.9 |
| 26 | 12.7 |
| 30 | 10.1 |
| 31 | 5.9 |
| 33 | 47.6 |
| 35 | NA |
| 41 | 27.1 |
| 45 | 8.9 |

TABLE 4-continued $EC_{50}$ Values of Various N-Acyloxazolidinones
$EC_{50}$ values of each compound with respect to the defective phenotype at 72 hr following treatment, calculated from dose-response data using 5 different concentrations (with $n \geq 36$ embryos for each concentration). NA = no statistically significant biological activity at any concentration.

| Compound | $EC_{50}$ (µM) |
|---|---|
| 52 | 6.1 |
| 54 | 30.4 |
| 55 | NA |

Compound 17, the cis N-crotonyl isomer of compound 1, was essentially as active as compound 1 in the frog embryo. However, compounds of the present invention in which the N-acyl moeity was larger than the crotonyl displayed a reduced activity (compound 13, compound 15, compound 23, compound 33, compound 35, compound 41, compound 54, and compound 55). Some of these compounds also contain a less electrophilic $\alpha,\beta$-unsaturated bond.

In addition to an unsaturated N-acyl group of moderate size, hydrophobic substitutions on other positions of the oxazolidinone ring may affect activity. Compound 6, which possesses an N-crotonyl group, but no substituents on ring C4 or C5 positions, displayed reduced activity. The 4-methyl, 5-phenyl enantiomers, i.e., compound 25 and compound 26, both were highly potent, as was compound 45, the enantiomer of compound 1. These results suggest a tolerance for different stereochemistries at these positions. Treatment with each of the biologically active compounds resulted in defects in the embryos that were qualitatively similar to those caused by treatment with compound 1, suggesting intervenetion along common or overlapping biological pathways.

In summary, compounds of structural formula (I) exhibit specific inhibitory effects on gastrulation and neurulation in the frog embryo has been found. These compounds of structural formula (I) inhibit blastopore closure, anteroposterior elongation, development of the head and eyes, visceral organogenesis and yolk resorption. Between 9 and 12 hours after treatment of late blastula embryos with a present compound, the embryos become irreversibly committed to the defective phenotype.

Experimental Procedures

Cell culture conditions: Madin-Darby canine kidney (MDCK) cells (American Type Culture Collection cell line CCL-34) were cultured in Minimum Essential Medium (with Earle's balanced salts, non-essential amino acids, L-glutamine and sodium pyruvate) supplemented with 10% newborn calf serum at 37° C. and 5% carbon dioxide ($CO_2$). Main cultures were grown in either 25 $cm^3$ or 75 $cm^3$ tissue culture flasks with medium changes every two days. When cultures were about 75% confluent, cells were passaged by rinsing twice with single strength phosphate buffered saline (PBS) and treating with a solution of 0.05% (w/v) trypsin/0.02% (w/v) ethylenediaminetetraacetic acid (EDTA) in PBS to detach cells from the flasks. After cells were detached, an equal volume of serum-containing medium was added to inhibit the trypsin and cell density was determined using a hemacytometer. Cells were replated following dilution in fresh medium on new tissue culture flasks for continued culture and multiwell tissue culture plates for experiments. No culture used exceeded 15 passages. Experimental cultures were grown in 12-, 24-, 48-, or 96-well tissue culture plates with medium changes every two days.

Wound closure assay and compound screening: MDCK cells were plated on multiwell tissue culture plates and cultured at 37° C. and 5% $CO_2$ with medium changes every two days until confluent. When the cultures reached confluence, medium was changed again and all experimental treatments were begun a day later. Compounds were solubilized in dimethyl sulfoxide (DMSO) and added with fresh-medium to cell cultures at initial screening concentrations of 10 and 100 μM. Controls consisted of parallel wells to-which DMSO solvent carrier alone was added at the same concentration as that added with experimental treatments (not exceeding 0.1% (v/v)). DMSO alone at this concentration had no detectable effect on the cells. Monolayers were scraped 30 min later with a micropipette and ultramicro tips, allowing small wounds of consistent size to be generated. Progress of wound closure was examined at set time intervals following wounding by microscope, and inhibitory or acceleratory effects on wound closure relative to parallel controls noted. Compounds that exhibited biological activity then were tested further at a range of concentrations with greater sample size. Digital images of the wounded monolayers were taken every 2 hours for 18 hours, and then at 30, 36, 54, 60, and 72 hours following wounding. The number of lamellipodia at the wound margin was also counted at these times.

Imaging and analysis: Wound closure assays were performed using either a Zeiss Axiovert 200 inverted microscope with a Zeiss AxioCam CCD camera and Improvision Open-Lab image software running on an Apple Power Mac G4 computer or a Zeiss Axiovert 25 inverted microscope with a Roper Scientific/Photometrics CoolSNAP-Pro CCD camera and Roper Scientific/Photometrics RS Image software on an Apple Power Mac G4 computer. Subsequent morphometric analyses using the digital images were performed using the public domain NIH Image program (developed at the U.S. National Institutes of Health and available on the Internet at http://rsb.info.nih.gov/nih-image/). These analyses entailed tracing the wound margin in each of the digital images to determine the length of the margin perimeter and the remaining open area. Microsoft Excel and GraphPad Prism software were used for routine tabulation, analysis and graphing of the data. The dose-response data was used to determine the $IC_{50}$ for inhibition of wound closure by compound 1 using GraphPad Prism software.

Filamentous actin staining: MDCK cell mono-layers on glass coverslips-were fixed with 3.7% formaldehyde in PBS 12 hours after wounding. Cells were permeabilized with 0.1% (w/v) TRITONO X-100 in PBS, stained with 50 nM tetramethylrhodamine-conjugated phalloidin in PBS, and washed twice with PBS. Coverslips were mounted in 90% glycerol/10% ten strength PBS with 2 mg/mL p-phenylenediamine on glass slides and then examined by fluorescence microscopy.

MDCK cell proliferation: MDCK cells were plated on multiwell tissue culture plates at low density ($1 \times 10^4$ cells/L). Cells were allowed to attach and begin to grow for 48 hours before the start of the experiment. Fresh medium with or without compound was then added, and cells were incubated for 48 hours. At both 0 and 48 hours, some of the parallel wells for control and compound treatments were washed twice with PBS and treated with trypsin/EDTA solution to detach the cells. An equal volume of medium was added, cells were collected and counted using a hemacytometer. For reversibility, some of the parallel cultures for both control and compound treatments were grown another 48 hours after washing twice with PBS and replacing medium with fresh compound-free medium. At both the time of washing out and 48 hours later, some of the parallel wells for control and compound treatments were washed twice with PBS, detached from the plates with trypsin/EDTA solution, and the number of cells was counted.

Bacterial growth: *Staphylococcus aureus* or *Escherichia coli* (DH5a strain) were grown in Luria-Bertani (LB) medium for 12 hours at 37° C. in a shaking incubator. Dilutions into fresh LB medium with 0.1% DMSO (solvent carrier control) or 50 μM compound 1 were made to an absorbance at 600 nm ($A_{600}$) of about 0.1. Bacteria were incubated at 37° C. with shaking during the experiment, and $A_{600}$ measurements were made at set time intervals during log growth phase until the plateau phase was reached.

*Xenopus laevis* Manipulation and Embryo Preparation

Standard procedures were used in the care of animals, gamete preparation, fertilization of oocytes, and culture of embryos (B. K. Kay et al., Methods in Cell Biology, Volumn 36 (San Diego: Academic Press, Inc.) (1991)). In order to stimulate ovulation, female frogs were injected with 500 units of human chorionic gonadotropin (HCG). Eggs were squeezed from female frogs 12 hours later. Testes were removed from euthanized male frogs that had been primed with 50 units of HCG 4-6 hours earlier. The testes were stored at 4° C. in single strength Marc's Modified Ringer's solution with 50 μg/ml gentamycin and used for no more than 10 days. Small pieces of testes were macerated and spread over eggs for in vitro fertilization in Petri dishes. Fertilized eggs were placed in one-tenth strength Modified Barth's Saline (MBS) with 50 μg/ml gentamycin at constant temperature (19° C.) in a temperature-controlled incubator and development allowed to proceed under these conditions. Embryos were dejellied by briefly swirling them in a solution of 2% (w/v) L-cysteine, pH 8.0. The embryos then were rinsed extensively with one-tenth strength MBS to wash out the cysteine. Experiments were started within an hour of dejellying the embryos.

Assay Protocol

Experiments were carried out in 12-well flat-bottom polystyrene plates with 4-8 embryos per well in 1.0 ml of one-tenth strength MBS with 50 μg/ml gentamycin at 19° C. Staging of embryos was done according to the classification of Nieuwkoop and Faber. Embryos at stage 8.5-9 (late blastula stages prior to the debut of gastrulation at stage 10) or at the 2-cell stage (after the first cleavage division, Nieuwkoop and Faber stage 2), as indicated in the figures, were treated with a test compound or dimethylsulfoxide (DMSO) carrier solvent and maintained at 19° C. DMSO concentration did not exceed 0.1% (v/v) in any experiment. DMSO alone at this concentration had no detectable effect on the embryos. For compound 22 and compound 41, dimethylformamide (DMF) was used as solvent because these compounds were more soluble in DMF, with final concentration of solvent again not exceeding 0.1% (v/v) in any experiment. As with 0.1% DMSO, this concentration of DMF had no effect on development of the frog embryos. Each experiment was conducted in triplicate on at least three separate occasions for a total of 9 or more wells per treatment. Embryos were observed using a stereomicroscope and scored for defects or delayed development at set times (0, 3, 6, 9, 12, 24, 48, 72, and 96 hours) following treatment.

Scoring Method

A range of morphological criteria were used to score for defects in embryogenesis as a function of time after addition of small molecules to live intact embryos. These criteria included delayed blastopore closure, reduced anterior structures and microcephaly, delayed appearance or absence of eye pigmentation, overall shortness along the anteroposterior axis, bent axis, bent tail only, reduced posterior structures/ tail, malformed or reduced fins, delayed or failed neural tube closure (neural fold fusion), abnormal pigmentation pattern, ventral swelling (edema), and delayed or abnormal visceral organogenesis and yolk resorption. Scoring was done for all embryos in each well at the time of observation. Any dead embryos in a well were noted as such and not used for scoring defects. A separate record of lethality was maintained. Measurements of anteroposterior length from head to tail were made using an eyepiece reticle at the time of observation. If an embryo was not positioned well for accurate scoring, the plate was shaken gently or the embryo was carefully moved into a better position for observation using a hair loop. Digital images were taken for documentation purposes for each well using a CCD camera attached to the stereomicroscope. GraphPad Prism software was used to graph data, perform statistical analyses and calculate $EC_{50}$ values.

Obviously, many modifications and variations of the invention as hereinbefore set forth can be made without departing from the spirit and scope thereof, and, therefore, only such limitations should be imposed as are indicated by the appended claims.

What is claimed is:

1. A method of controlling progression of a cancer through metastasis in a male or female animal suffering from a colon cancer, lung cancer, or breast cancer comprising administering a therapeutically effective amount of (a) a compound having a formula

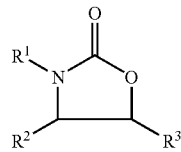

wherein $R^1$ is selected from the group consisting of $C(=O)$ $C_{3-8}$cycloalkenyl, $C(=O)C\equiv C-R^b$ and

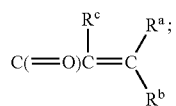

$R^2$ is selected from the group consisting of $C_{1-3}$alkyl and $C_{1-3}$alkylenearyl;
$R^3$ is selected from the group consisting of hydrogen and $C_{1-3}$alkyl;
$R^a$ is selected from the group consisting of hydrogen and $C_{1-3}$alkyl;
$R^b$ is selected from the group consisting of hydrogen and $C_{1-3}$alkyl;
$R^c$ is selected from the group consisting of hydrogen and $C_{1-3}$alkyl; or
a pharmaceutically acceptable salt thereof,
and (b) a second therapeutically active ingredient used in a treatment of the cancer, wherein the second therapeutically active ingredient is a chemotherapeutic agent or radiation.

2. The method of claim 1 wherein (a) and (b) are administered simultaneously or sequentially.

3. The method of claim 1 wherein the compound has a structure

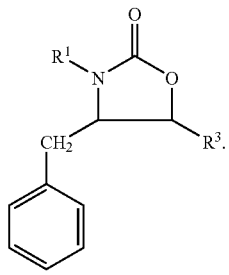

4. The method of claim 1 wherein the compound has a structure

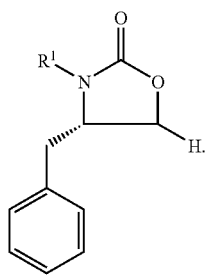

5. The method of claim 1 wherein the compound has a structure

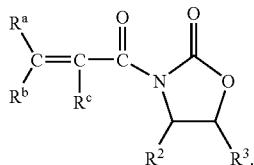

6. The method of claim 1 wherein $R^3$ is hydrogen; $R^2$ is selected from the group consisting of hydrogen, isopropyl, and methyl; $R^a$ is hydrogen or methyl; $R^b$ is selected from the group consisting of hydrogen, methyl, and ethyl.

7. The method of claim 1 wherein $R^2$ is selected from the group consisting of hydrogen, isopropyl, and methyl; and $R^1$ is selected from the group consisting of $-C(=O)$ $CH=CHCH_3$, $-C(=O)CH=CH_2$, $-C(=O)$ $CH=CHC_2H_5$,

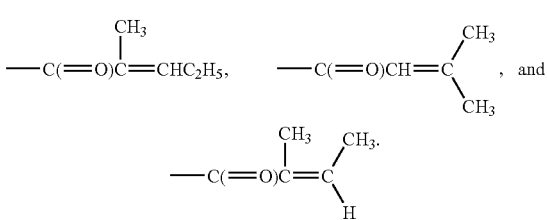

8. The method of claim 1 wherein the compound has a structure

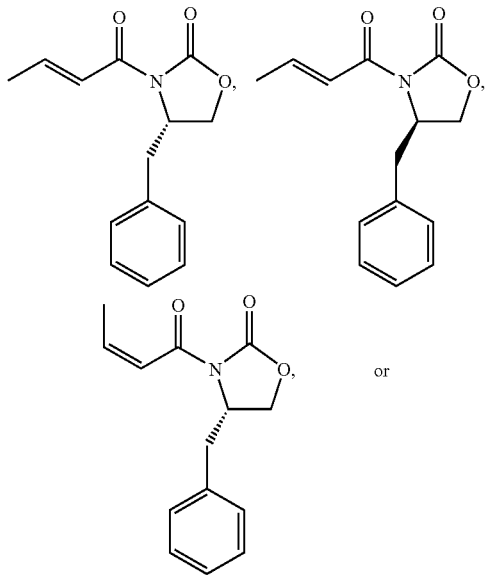

or

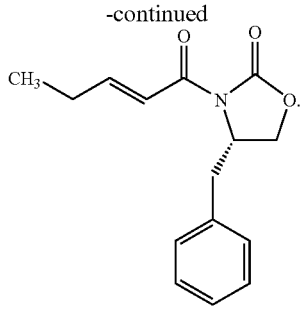

9. The method of claim 1 wherein the compound has a biological $IC_{50}$ value of about 50 μM or less.

10. The method of claim 1 wherein the compound is (4S)-3-((E)-2-butenoyl-4-benzyl-2-oxazolidinone.

11. The method of claim 1 wherein the second therapeutically active ingredient is a chemotherapeutic agent and the cancer is colon cancer, lung cancer, or breast cancer.

12. The method of claim 1 wherein the second therapeutically active ingredient is radiation, and the cancer is colon cancer, lung cancer, breast cancer, or rectal carcinoma.

* * * * *

UNITED STATES PATENT AND TRADEMARK OFFICE
CERTIFICATE OF CORRECTION

PATENT NO.        : 7,390,826 B2
APPLICATION NO.   : 11/259170
DATED             : June 24, 2008
INVENTOR(S)       : Gabriel Fenteany et al.

Page 1 of 1

It is certified that error appears in the above-identified patent and that said Letters Patent is hereby corrected as shown below:

On the Title Page:

Item (75), fourth named Inventor, "Audha Ankala" should be -- Sudha Ankala --.

Signed and Sealed this

Thirtieth Day of September, 2008

JON W. DUDAS
*Director of the United States Patent and Trademark Office*